United States Patent [19]

Osswald et al.

[11] Patent Number: 5,438,063

[45] Date of Patent: Aug. 1, 1995

[54] IMIDAZOPYRIDINES AS ANGIOTENSIN II ANTAGONISTS

[75] Inventors: Mathias Osswald, Zwingenberg; Werner Mederski, Erzhausen; Dieter Dorsch, Ober-Ramstadt; Pierre Schelling, Muhltal; Norbert Beier, Reinheim; Ingeborg Lues, Darmstadt; Klaus-Otto Minck, Ober-Ramstadt, all of Germany

[73] Assignee: Merck Patent Gesellschaft Mit Beschrankter Haftung, Darmstadt, Germany

[21] Appl. No.: 254,834

[22] Filed: Jun. 6, 1994

[30] Foreign Application Priority Data

Jun. 7, 1993 [DE] Germany .................. 43 18 813.3

[51] Int. Cl.$^6$ ............... A61K 31/435; C07D 471/04
[52] U.S. Cl. ................. 514/303; 514/234.2; 544/127; 546/118
[58] Field of Search ............ 546/118; 514/303, 234.2; 544/127

[56] References Cited

U.S. PATENT DOCUMENTS

| | | | |
|---|---|---|---|
| 4,880,804 | 11/1989 | Carini et al. | 514/234.5 |
| 5,223,499 | 6/1993 | Greenlee | 514/234.5 |
| 5,242,928 | 9/1993 | Mederski | 514/303 |
| 5,243,054 | 9/1993 | Naka et al. | 548/132 |
| 5,332,744 | 7/1994 | Chakravarty | 514/261 |

FOREIGN PATENT DOCUMENTS

| | | |
|---|---|---|
| 0400974 | 12/1990 | European Pat. Off. . |
| 0430709 | 6/1991 | European Pat. Off. . |
| 0505893 | 9/1992 | European Pat. Off. . |
| 0520423 | 12/1992 | European Pat. Off. . |

OTHER PUBLICATIONS

Wong, The Journal of Pharmacology and Experimental Therapeutics, vol. 252, No. 2, pp. 719–725 (1990).
Chiu, The Journal of Pharmacology and Experimental Therapeutics, vol. 250, No. 3, pp. 867–874 (1989).

*Primary Examiner*—Ceila Chang
*Assistant Examiner*—Evelyn Huang
*Attorney, Agent, or Firm*—Millen, White, Zelano & Branigan

[57] ABSTRACT

Novel imidazopyridine derivatives of formula I

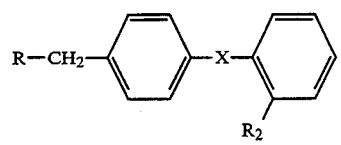

wherein

R is 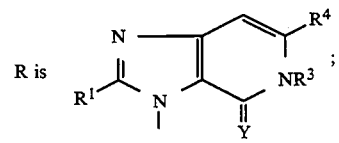

and $R^1$, $R^2$, $R^3$, $R^4$, X and Y are as defined herein, and their salts, exhibit antagonistic properties toward angiotensin II and can be used for the treatment of hypertension, aldosteronism, cardiac insufficiency and increased intraocular pressure, and of disorders of the central nervous system.

30 Claims, No Drawings

IMIDAZOPYRIDINES AS ANGIOTENSIN II ANTAGONISTS

SUMMARY OF THE INVENTION

The invention relates to novel imidazopyridine derivatives of the formula I:

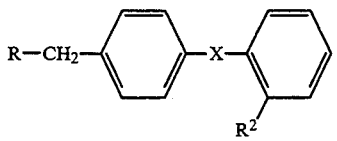

wherein
R is

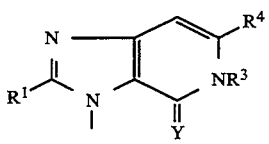

$R^1$ is A, $C_2$-$C_6$-alkenyl, $C_2$-$C_6$-alkynyl, $C_3$-$C_8$-cycloalkyl-$C_kH_{2k}$-, or $C_1$-$C_6$-alkyl in which a $CH_2$ group is replaced by O or S, $R^2$ is -$SO_2$NH-$COOR^5$, -$SO_2$NH-$COR^5$, -$SO_2$NH-$SO_2R^5$, -$SO_2$NH-$CONR^5R^6$, -C($NH_2$)=NOH, 4,5-dihydro-5-oxo-1,2,4-oxadiazol-3-yl, 4,5-dihydro-5-thioxo-1,2,4-oxadiazol-3-yl, 2-oxo-3H-1,2,3,5-oxathiadiazol-4-yl, 2,2-dioxo-3H-1,2,3,5-oxathiadiazol-4-yl, 2,3-dihydro-3-oxo-1,2,4-oxadiazol-5-yl, 2,5-dihydro-2,5-dioxo-1H-imidazol-4-yl, 4,5-dihydro-5-oxo-1H-1,2,4-triazol-3-yl, 4,5-dihydro-5-thioxo-1H,1,2,4-triazol-3-yl, 2,3-dihydro-2-oxo-1,3,4-thiadiazol-5-yl or 4,5-dihydro-5-oxo-1,2,4-thiadiazol-3-yl, $R^3$ is H, $R^{11}$, $C_2$-$C_6$-alkenyl, unsubstituted, monosubstituted or polysubstituted by COOH, COOA, CN, $NO_2$, $NR^9R^{10}$, $NHCOR^{11}$, $NHSO_2R^{11}$, Hal and/or Ar, or is $C_2$-$C_6$-alkynyl, -$C_nH_{2n}$-$R^{12}$, -$CHR^{13}$-$C_kH_{2k}$-$R^{14}$ or

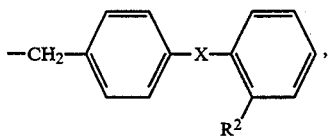

$R^4$ is H or Hal, $R^5$ and $R^6$ are each H, a $C_1$-$C_6$-alkyl group, wherein one $CH_2$ group can also be replaced by O or S or an additional C-C double bond can be contained and which can additionally be substituted by ON, $OR^7$, Ar, $Het^2$, $NR^7R^8$, $NR^7$-$COOR^8$, $NR^7$-$COO$-$C_tH_{2t}$-Ar, $NR^7$-$COO$-$C_tH_{2t}$-$Het^2$ and/or $COOR^7$, or are $C_3$-$C_8$-cycloalkyl, $CF_3$, Ar or $Het^2$, $R^7$ and $R^8$ are each A, $C_2$-$C_6$-alkenyl, $C_2$-$C_6$-alkynyl, $C_3$-$C_8$-cycloalkyl-$C_kH_{2k}$- or $C_1$-$C_6$-alkyl, wherein one $CH_2$ group is replaced by O or S, $R^9$ and $R^{10}$ are each H, A, $C_2$-$C_6$-alkenyl or $C_2$-$C_6$-alkynyl, Ar, $ArC_nH_{2n}$- or $Het^2$, $R^9$ is also -$CH_2$COOA, -$SO_2$-A or -$SO_2$-Ar, $R^9$ and $R^{10}$ together are also an alkylene chain having 2-5 C atoms, which can be mono-substituted or poly-substituted by carbonyl oxygen, Ar, $Het^2$ -CO-Ar -COOA, -CO-N(A)$_2$, -$CH_2$OH, -$SO_2$-Ar and/or -NH-CO-A and/or interrupted by O or by -$NR^{19}$-, $R^{11}$ is $C_1$-$C_5$-alkyl, wherein one or more H atoms can be replaced by F, $R^{12}$ is $C_3$-$C_8$-cycloalkyl, CN, COOA, COON, Ar, $Het^1$, $Het^2$, 1H-tetrazol-5-yl, -CO-$NR^9R^{10}$, -CO-$R^{11}$, -CO-Ar, -CO-$Het^2$-CO-$R^{17}$, -C(=$NR^{15}$)-A, -C(=$NR^{15}$)-$Het^2$-S(O)$_m$-A, -S(O)$_m$-Ar, -S(O)$_m$-$Het^2$, -$SO_2$-NH-$Het^2$ or -$SO_2$-$OR^{18}$, $R^{13}$ is COOH, COOA, $CONR^9R^{10}$, CN, $NO_2$, $NHCOR^{14}$, $NHSO_2R^{14}$ or 1H-tetrazol-5-yl, $R^{14}$ is Ar or cycloalkyl having 3-8 C atoms, $R^{15}$ is H, OH, CN, $R^{16}$, $OR^{16}$ or OAr, $R^{16}$ is A, $C_2$-$C_6$-alkenyl or $C_2$-$C_6$-alkynyl, $R^{17}$ is -NH-$CHR^{18}$-COOH, -NH-$CHR^{18}$-COOA, -$CH_2$S (O)$_m$-Ar, -$CH_2$-COOA, -$C_nH_{2n}$-$NO_2$, -$C_nH_{2n}$-$NR^9R^{10}$ or -$C_nH_{2n}$-NHCOOA, $R^{18}$ is H or A, $R^{19}$ is H, A, Ar, COOA, $Het^2$ or $SO_2$-Ar, X is absent or is -NH-CO- or -CO-NH-, Y is O or S, A is $C_1$-$C_6$-alkyl, Ar is an unsubstituted phenyl group or a phenyl group monosubstituted or disubstituted by $R^{11}$, OH, $OR^{11}$, COOH, COOA, CN, $NO_2$, $NH_2$, NHA, N(A)$_2$, $NHCOR^{11}$, NHCOOA, $NHSO_2R^{11}$, Hal and/or 1H-tetrazol-5-yl, $Het^1$ is a five- or six-membered saturated heterocyclic radical having 1 to 3 N, O and/or S atoms, which can be monosubstituted by carbonyl oxygen or =$NR^{15}$ and/or whose ring N atom(s) can in each case be substituted by A or Ar, $Het^2$ is a five- or six-membered heteroaromatic radical having 1 to 3 N, O and/or S atoms, which is unsubstituted or substituted by one or more A groups and/or which can be fused with a benzene or pyridine ring, Hal is F, Cl, Br or I, k is 0, 1, 2, 3 or 4, m is 0, 1 or 2, n is 1, 2, 3, 4, 5 or 6 and t is 1, 2, 3 or 4, and their salts.

Similar compounds are known from European patent application A2-0 400 974.

An object of the invention is to provide novel compounds with valuable properties, especially compounds which can be used for the preparation of drugs.

Upon further study of the specification and appended claims, further objects and advantages of this invention will become apparent to those skilled in the art.

It has been found that the compounds of the formula I and their salts possess very valuable pharmacological properties coupled with a good tolerance. In particular, they exhibit antagonistic properties towards angiotensin II and can therefore be used as pharmaceutically active ingredients for the prophylaxis and/or therapy of coronary, cardiovascular and vascular disorders, in particular for the treatment of angiotensin II-dependent hypertension, aldosteronism, cardiac insufficiency and increased intraocular pressure, and of disorders of the central nervous system, also of hypertrophy and hyperplasia of the blood vessels and of the heart, angina pectoris, cardiac infarct, stroke, restenoses after angioplasty or by-pass operations, arteriosclerosis, glaucomas, macular degeneration, hyperuricaemia, kidney function disorders, e.g., kidney failures, diabetic nephropathy, diabetic retinopathy, psoriasis, angiotensin II-mediated disorders in female reproductive organs, perceptive disorders, e.g., dementia, amnesia, memory function disorders, anxiety states, depression and/or epilepsy.

These effects can be determined by conventional in vitro or in vivo methods such as, for example, those described in U.S. Pat. NO. 4,880,804, U.S. Pat. No. 5,036,048 and International Patent Application 91/14367 and also by A. T. Chiu et al., J. Pharmacol. Exp. Therap. 250, 867–874 (1989), and by P. C. Wong et al., ibid. 252, 719–725 (1990; in vivo, on rats).

The invention relates to the compounds of the formula I and their salts and to a process for the preparation of these compounds and their salts, characterized in that (a) a compound of the formula II

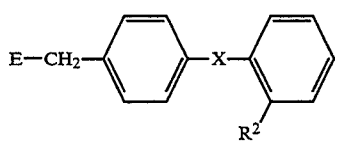

wherein

E is Cl, Br, I, a free OK group or an OK group which has been functionally modified to acquire reactivity, and $R^2$ and X are as defined in formula I, is reacted with a compound of the formula III

H-R      III wherein

R is as defined in formula I, or (b) a compound of the formula IV

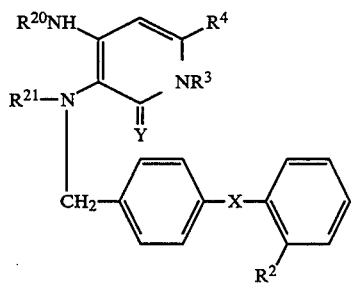

wherein $R^{20}$ is $R^1$-CO or H and $R^{21}$ is H (if $R^{20}$ is $R^1$-CO) or $R^1$-CO (if $R^{20}$ is H), and $R^1$, $R^2$, $R^3$, $R^4$, X and Y are as defined in formula I is treated with a cyclizing agent, or (c) to prepare a compound of the formula I wherein X is -NH-CO- or -CO-NH-, a compound of the formula V

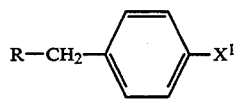

wherein $X^1$ is $NH_2$ or COOH, and

R is as defined in formula I, or a reactive derivative of this compound, is reacted with a compound of the formula VI

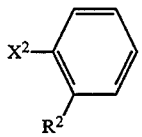

wherein $X^2$ is COOH (if $X^1$ is $NH_2$) or $NH_2$ (if $X^1$ is COOH), and $R^2$ is as defined in formula I, or with a reactive derivative of this compound, or (d) to prepare a compound of the formula I wherein $R^2$ is -C($NH_2$)=NOH, a compound which corresponds to formula I but the radical $R^2$ is replaced by a CN group, is reacted with hydroxylamine or (e) to prepare a compound of the formula I wherein $R^2$ is -$SO_2$NH-$COOR^5$, -$SO_2$NH-$COR^5$, -$SO_2$NH-$SO_2R^5$ or -$SO_2$NH-$CONR^5R^6$, a compound, which corresponds to the formula I but in which the radical $R^2$ is replaced by an -$SO_2NH_2$ group, is reacted with a compound of the formula E-$COOR^5$, E-$SO_2R^5$, E-$CONR^5R^6$ or O=C=$NR^5$ or (f) a compound of the formula I is freed from one of its functional derivatives by treatment with a solvolyzing or hydrogenolyzing agent, and/or in that one or more radicals R, $R^2$ and/or in a $R^3$ in a compound of the formula I are converted to one or more different radicals R, $R^2$ and/or $R^3$ and/or a base or acid of the formula I is converted to one of its salts.

Above and below, unless expressly indicated othewise, the radicals or parameters R, $R^1$ to $R^{21}$, X, Y, A, Ar, $Het^1$, $Het^2$, Hal, k, m, n, t, E, $X^1$ and $X^2$ are as defined in formulae I to VIII.

In the above formulae, A has 1–6, preferably 1, 2, 3 or 4 C atoms. A is preferably methyl, or else ethyl, propyl, isopropyl, butyl, isobutyl, sec-butyl or tertbutyl, or else pentyl, 1-, 2- or 3 -methylbutyl, 1,1-, 1,2 - or 2,2-dimethylpropyl, 1-ethylpropyl, hexyl, 1-, 2-, 3- or 4 -methylpentyl, 1,1-, 1,2 -, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, prop- 1-enyl, prop-2-enyl or but-1-enyl, or else pent-1-enyl or hex- 1 -enyl. Alkynyl is preferably ethynyl, prop- 1 -ynyl or prop-2-ynyl, or else but-1-ynyl, pent-1-ynyl or hex-1-ynyl. If several radicals A, alkenyl or alkynyl are present in a compound of the formula I, they can be identical to or different from one another.

Hal is preferably F, Cl or Br, or else I.

R is a radical derived from 3H-imidazo[4,5-c]pyridine ("3H-IP") or, more precisely, 2-$R^1$-4- (thi)oxo-5-$R^3$-6-$R^4$-4,5-dihydro-3H -imidazo[4,5-c]pyridin-3-yl.

Ar is preferably unsubstituted or further, as indicated, monosubstituted phenyl; in detail preferably phenyl, o-, m- or p-tolyl, o-, m- or p-ethylphenyl, o-, m- or p-trifluoromethylphenyl, o-, m- or p-methoxyphenyl, o-, m- or p-ethoxyphenyl, o, m- or p-difluoro-methoxyphenyl, o-, m- or p-trifluoromethoxyphenyl, o-, m- or p-carboxyphenyl, o-, m- or p-methoxycarbonylphenyl, o-, m-or p-ethoxycarbonylphenyl, o-, m- or p-cyanophenyl, o-, m- or p-nitrophenyl, o-, m- or p-aminophenyl, o-, m- or p-methylaminophenyl, o-, m- or p-dimethylaminophenyl, o-, m- or p-trifluoroacetamidophenyl, o-, m- or p-methoxycarbonylamino, o-, m- or p-ethoxycarbonylamino, o-, m- or p-methylsulfonamidophenyl, o-, m- or p-trifluoromethylsulfonamidophenyl, o-, m- or p-fluorophenyl, o-, m- or p-chlorophenyl, o-, m- or p-bromophenyl, o-, m- or p- (1H-tetrazol-5-yl)phenyl, furthermore preferably 2,3-, 2,4-, 2,5-, 2,6-, 3,4- or 3,5-dimethylphenyl, 2,3- 2,4-, 2,5-2,6-, 3,4- or 3,5-dimethoxyphenyl.

$Het^1$ is preferably tetrahydro-2- or -3-furyl, tetrahydro-2- or -3-thienyl, 1-, 2-, 3- or 3-pyrrolidinyl, 2-, 3-, 4- or 5-oxazolidinyl, 2-, 3-, 4 - or 5-thiazolidinyl, 1-, 2-, 3-, 4-or 5-imdazolidinyl, 2-, 3- or 4-tetrayhydropyranyl, 2-, 3- or 4-tetrahydrothiopyranyl, 1-, 2 -, 3- or 4-piperidinyl, 2-, 3- or 4 -morpholinyl, 1-, 2- or 3-piperazinyl, 1-methyl-2 - or -3 -pyrrolidinyl, 1-methyl-2-, -3- or -4-piperidinyl, 4 -methyl-2- or -3-morpholinyl, 1-methyl-2-, -3- or -4-piperazinyl, 1-phenyl-2- or -3-pyrrolidinyl, 1-phenyl-2-, -3- or -4-piperidinyl, 4 -phenyl-2- or -3-morpholinyl, 1-phenyl-2 -, -3- or 4-piperazinyl, 2-oxo-3-, -4- or -5-oxazolidinyl, 2-oxo-3-, -4- or -5-thiazolidinyl, 2-oxo-1-, -3-, -4- or -5-imidazolidinyl, 2,4-dioxo-1-, -3- or -5-imidazolidinyl, 2-oxo-3-phenyl-4- or -5-oxazolidinyl, 2-oxo-3-o-, -m- or -p-tolyl-4- or -5-oxazolidinyl, 2-hydroxyimino-3-, -4- or -5-oxazolidinyl, 2-methoxyimino-3-, -4- or -5-oxazolidinyl, 2-hydroxyimino-4-oxo-3- or -5-oxazolidinyl, 2-methoxyimino-4-oxo-3- or -5-oxazolidinyl.

$Het^2$ is preferably furan-2- or -3-yl, thien-2- or -3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or -5-yl, thiazol-2-, -4- or -5-yl, isothiazol-3-, -4- or -5-yl, pyridin-2-, -3- or -4-yl or pyrimidin-2-, -4-, -5- or -6-yl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -4-yl, 2,1,5-thiadiazol-3- or -4-yl, pyridazin-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6or -7-yl, benzimidazol-1-, -2-, -4- or -5-yl, benzopyrazol-1-, -3-, -4-, -5-, -6- or -7-yl, benzoxazol-2-, -4, -5-, -6- or -7-yl, benzisoxazol-3-, -4-, -5-, -6- or -7-yl, benzothiazol-2-, -4-, -5-, -6- or -7-yl, benzisothiazol-2-, -4-, -5-, -6- or -7-yl, benz-2,1,3-oxadiazol-4-, -5-, -6- or -7-yl, quinol-2-, -3-, -4-, -5-, -6-, -7- or -8-yl, isoquinol-1-, -3-, -4-, -5-, -6-, -7- or -8-yl, cinnolin-3-, -4-, -5-, -6-, -7- or -8-yl, quinazol-2-, -4-, -5-, -6-, -7- or -8-yl, 1H-imidazo-[4,5-b]pyridin-1-, -2-, -5-, -6- or -7-yl, 3-imidazo [4,5-b]pyridin-2-, -3-, -5-, -6- or -7-yl, 1H-imidazo [4,5-c]pyridin-1-, -2-, -4-, -6- or -7-yl or 3H-imidazo [4,5-c]pyridin-2-, -3-, -4-, -6- or -7-yl.

The term "$Het^2$" also includes the homologous radicals in which the heteroaromatic ring is substituted by one or more, preferably 1 or 2 groups A, preferably methyl and/or ethyl groups, for example 3-, 4- or 5-methylfuran-2-yl, 2-, 4- or 5-methylfuran-3-yl, 2,4-dimethylfuran-3-yl, 3-, 4- or 5-methylthien-2-yl, 3-methyl-5-tert-butylthien-2-yl, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-l-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4-dimethylthiazol-5-yl, 3-, 4-, 5- or 6-methylpyridin-2-yl, 2-, 4-, 5- or 6-methylpyridin-3-yl, 2- or 3-methylpyridin-4-yl, 4-methylpyrimidin-2-yl, 4,5-dimethylpyrimidin-2-yl, 2-, 5- or 6-methylpyrimidin-4-yl, 2,6-dimethylpyrimidin-4-yl, 3-, 4-, 5-, 6- or 7-methylbenzofuran-2-yl, 2-ethylbenzofuran-3-yl, 3-, 4-, 5-, 6or 7-methylbenzofuran-2-yl, 3-ethylbenzothien-2-yl, 1-, 2-, 4-, 5-, 6- or 7-methylindol-3-yl, 1-methylbenzimidazol-5 - or -6-yl or 1-ethylbenzimidazol-5- or -6-yl.

The groups -$C_kH_{2k}$-, -$C_nH_{2n}$- and $C_tH_{2t}$ are preferably straight-chain and are thus preferably -$(CH_2)_n$-, -$(CH_2)_k$- and -$(CH_2)_r$, in particular -$CH_2$-, also -$CH_2CH_2$-, -$(CH_2)_3$-, -$(CH_2)_4$-, -$(CH_2)_5$- or -$(CH_2)_6$-, but also, for example, -$CH(CH_3)$-, -$CH_2$-$CH(CH_3)$- or -$C(CH_3)_2$-. The parameter k can preferably also be 0, so that the group -$C_kH_{2k}$- is absent.

The radical $R^1$ is preferably straight-chain and is preferably A, in particular ethyl, propyl or butyl, also methyl, pentyl or hexyl, and also cycloalkyl having 3–7 C atoms, in particular cyclopropyl, also cyclobutyl, cyclopentyl, cyclohexyl, cycloheptyl, furthermore in particular alkenyl preferably having 3–6 C atoms, in particular allyl or 1-propenyl, also 1-butenyl, 1-pentenyl or 1-hexenyl; alkynyl preferably having 3–6 C atoms, in particular propargyl or 1-propynyl, also 1-butynyl, 1-pentynyl or 1-hexynyl; cycloalkylalkyl preferably having 4–8 C atoms, in particular cyclopropylmethyl, 1- or 2-cyclopropylethyl, also cyclobutylmethyl, cyclopentylmethyl, cyclohexylmethyl; alkoxy preferably having 1–4 C atoms, such as methoxy, ethoxy, propoxy, butoxy, isobutoxy; alkoxyalkyl preferably having 2–5 C atoms, such as methoxymethyl, ethoxymethyl, propoxymethyl, 2-methoxyethyl, 3-methoxypropyl, 2-ethoxyethyl; alkylthio preferably having 1–4 C atoms such as methylthio, ethylthio, propylthio, butylthio, isobutylthio; alkylthioalkyl preferably having 2–5 C atoms such as methylthiomethyl, ethylthiomethyl, propylthiomethyl, 2-methylthioethyl, 3-methylthiopropyl and 2-ethylthioethyl.

The radical $R^2$ is preferably -$SO_2NH$-$COOR^5$ in particular -$SO_2NH$-$COOA$; -$SO_2NH$-$CO$-$R^5$, in particular -$SO_2NH$-$COAr$ such as -$SO_2NH$-$COC_6H_5$;-$SO_2NH$-$CONR^5R^6$,in particular -$SO_2NH$-$CO$-$NHAr$ such as -$SO_2NH$-$CO$-$NHC_6H_5$ or -$SO_2NH$-$CO$-$NHC_2Het^2$ such as -$SO_2NH$-$CO$-$NHCH_2$-(2-pyridyl). The radical $R^2$ is further preferably 4,5-dihydro-5-oxo-1,2,4-oxadiazol-3-yl, or further preferably 4,5-dihydro-5-thioxo-1,2,4-oxadiazol-3-yl, 2-oxo-3H-1,2,3,5-oxathiadiazol-4yl, 2,2-dioxo-3H-1,2,3,5-oxathiadiazol-4-yl or 4,5-dihydro-5-oxo-1,2,4 -thiadiazol-3-yl.

The radical $R^3$ is preferably H; $R^{11}$, in particular $CH_3$, $CF_3$, $C_2F_5$, $CH_2CF_3$, $CH_2CH_2CF_3$; Ar-$C_2$-$C_6$-alkenyl, for example cinnamyl; Ar-$C_2$-$C_6$-alkenyl substituted in the "alkenyl" moiety by COOA, for example 3-ethoxycarbonyl-2-phenyl-2-propen-1-yl; -$C_nH_{2n}$-$R^{12}$ (in detail preferably $CH_2$-$R^{12}$), in particular -$C_n$-$H_{2n}$-$C_3$-$C_8$-cycloalkyl -(such as), cyclopropylmethyl, cyclobutylmethyl, cyclopentylmethyl, cyclohexylmethyl) , -$C_nH_{2n}$-CN (such as cyanomethyl, 2-cyanoethyl, 3-cyanopropyl), -$C_nH_{2n}$-COOA (such as methoxycarbonylmethyl, ethoxycarbonylmethyl, 2-methoxycarbonylethyl, 2-ethoxycarbonylethyl) , -$C_nH_{2n}$-COOH (such as carboxymethyl, 2-carboxyethyl, 3-carboxypropyl) , -$C_nH_{2n}$-Ar (such as benzyl, 1- or 2-phenylethyl, 1-, 2- or 3-phenylpropyl, 1-, 2 -, 3- or 4-phenylbutyl, o-, m- or p-fluorobenzyl, (preferably) o-, m- or p-chlorobenzyl, o-, m- or p-bromobenzyl, o-, m- or p-methylbenzyl, o-, m- or p-trifluoromethylbenzyl, o-, m- or p-methoxycarbonylbenzyl, o-, m- or p-ethoxycarbonylbenzyl, o-, m- or p-cyanobenzyl, o-, m- or p-carboxybenzyl, o-, m- or p-nitrobenzyl, o-, m- or p-aminobenzyl, o-, m- or p-trifluoroacetamidobenzyl, o-, m- or p-trifluoromethylsulfonamidobenzyl, o-, m- or p- (1H-tetrazol-5-yl) benzyl, 2-chloro-6-nitrobenzyl); -$C_nH_{2n}$-

Het¹ (preferably -CH$_2$-Het¹ such as -CH$_2$- (2-oxo-3-Ar-5-oxazolidinyl), for example 2-oxo-3-m-tolyl-5-oxazolidinylmethyl); -C$_n$H$_{2n}$-Het² (preferably -CH$_2$-Het² such as 2- or 3-furylmethyl, 2- or 3-thienylmethyl, 5-isoxazolylmethyl, 5-methyl-3-isoxazolylmethyl, 2-, 3- or 4 - pyridylmethyl, pyrazinylmethyl, 2-, 4-, 5- or 6-pyrimidinylmethyl, 3- or 4-pyridazinylmethyl, 2-, 3-, 4 -, 5-, 6- or 7-benzofurylmethyl, 2-, 3-, 4-, 5-, 6- or 7-benzothienylmethyl, 2-, 3-, 4-, 5-, 6- or 7 -indolylmethyl); -C$_n$H$_{2n}$-(1H-tetrazol-5-yl ) (such as 1H-tetrazol-5-ylmethyl, 2-(1H-tetrazol-5-yl)ethyl, 3-(1H-tetrazol-5-yl)propyl); -C$_n$H$_{2n}$-CONR⁹R¹⁰ (in which n is preferably 1 or 2, R⁹ is preferably H or A and R¹⁰ is preferably H, A, Ar, ArC$_n$H$_{2n}$ or Het², such as carbamoylmethyl, 2-carbamoylethyl, N-methylcarbamoylmethyl, 2-N-methylcarbamoylethyl, N-ethyl-carbamoylmethyl, N-propyl-carbamoylmethyl, N-isopropyl-carbamoylmethyl, N-butyl-carbamoylmethyl, N-isobutyl-carbamoylmethyl, N-sec-butyl-carbamoylmethyl, N-tert-butyl-carbamoylmethyl, N,N-dimethyl-carbamoylmethyl, 2 -N , N-dimethyl-carbamoylethyl, N-methyl-N-ethylcarbamoylmethyl, N,N-diethyl-carbamoylmethyl, N,N-dipropyl-carbamoylmethyl, N,N-diisopropyl-carbamoylmethyl, N,N-dibutyl -carbamoylmethyl; further, for example, pyrrolidinocarbonylmethyl, piperidinocarbonylmethyl, morpholinocarbonylmethyl); -C$_n$H$_{2n}$-CO-NHAr, for example, N-phenylcarbamoylmethyl, 2 -N-phenyl-carbamoylethyl, N-o-, -m- or -p-tolyl-carbamoylmethyl, N-o-, m- or -p-trifluoromethylphenyl-carbamoylmethyl, N-o-, -m- or -p-carboxyphenyl-carbamoylmethyl, N-o-, -m- or -p-ethoxy-carbonyl-phenyl-carbamoylmethyl, N-o-, -m- or p-fluoro-phenyl-carbamoylmethyl, N-o-, -m- or -p-chlorophenylcarbamoylmethyl, N-(2,3-, N-(2,4-, N-(2,5-, N-(2,6-, N-(3,4- or N-(3,5-dimethylphenyl)-carbamoylmethyl, 2-N-(2,3-, 2-N-(2,4-, 2-N-(2,5-, 2-N-(2,6-, -2-N-(3,4- or 2-N-(3,5-dimethylphenyl)-carbamoylethyl; -C$_n$H$_{2n}$-CO-NH-Het², for example, N-(2-, N-(3-, or N-(4-pyridyl) -carbamoylmethyl, 2-N-(2-pyridyl)-carbamoylethyl, N-(2- or N-(3-thienyl)-carbamoylmethyl; -C$_n$H$_{2n}$-CO-NAAr, for example, N-methyl-N-phenyl-carbamoylmethyl, 2 -N-methyl-N-phenylcarbamoylethyl, N-ethyl-N-phenyl-carbamoylmethyl; -C$_n$H$_{2n}$-CO-NA(C$_n$H$_{2n}$-AR), for example, N-methyl-N-benzyl-carbamoylmethyl, N-methyl-N-(2-phenylethyl)-carbamoylmethyl, N-methyl-N-(1,1-dimethyl-2-phenylethyl)-carbamoylmethyl, 2-N-methyl-N-(1,1-dimethyl-2-phenylethyl)-carbamoylethyl; -C$_n$H$_{2n}$-CO-N(Ar)$_2$, for example, N,N-diphenylcarbamoylmethyl; -C$_n$H$_{2n}$-CO-R¹¹ (preferably -CH$_2$-CO-R¹¹ such as 2-oxopropyl, 2-oxobutyl, 3-methyl-2-oxobutyl, 3,3-dimethyl-2-oxobutyl, 3,3,3-trifluoro-2-oxopropyl, 3,3,4,4,4-pentafluoro-2-oxobutyl); -C$_n$H$_{2n}$-CO-Ar (preferably CH$_2$-CO-Ar such as phenacyl (=2-oxo-2-phenylethyl) , o-, m- or p-methylphenacyl, o-, m- or p-ethylphenacyl, o-, m- or p-trifluoromethylphenacyl, o-, m-or p-methoxyphenacyl, o-, m- or p-ethoxyphenacyl, o-, m- or p-(difluoromethoxy)-phenacyl, o-, m- or p-(trifluoromethoxy)phenacyl, o-, m or p-carboxyphenacyl, o-, m- or p-methoxycarbonylphenacyl, o-, m-or p-ethoxycarbonylphenacyl, o-, m-or p-cyanophenacyl, o-, m- or p-nitrophenacyl, o-, m- or p-aminophenacyl, o-, m- or p-acetamidophenacyl, o-, m- or p-trifluoroacetamidophenacyl, o-, m- or p-methylsulfonamidophenacyl, o-, m- or p-trifluoromethylsulfonamidophenacyl, o-, m- or p-(1H-tetrazol-5-yl)phenacyl; -C$_n$H$_{2n}$-CO-Het² (preferably -CH$_2$-CO-Het² such as 2 -furoylmethyl, 3-thenoylmethyl, picolinoylmethyl, nicotinoytmethyl, isonicotinoylmethyl, pyrazinecarbonylmethyl, 2-, 4-, 5- or 6-pyrimidinecarbonylmethyl, 3- or 4-pyridazinecarbonylmethyl, benzofuran-2-, -3-, -4-, -5-, -6- or -7-carbonylmethyl, benzothiophene-2-, -3-, -4-, -5-, -6- or -7-carbonylmethyl, indol-2-, -3-, -4-, -5-, -6- or -7-carbonylmethyl); -C$_n$H$_{2n}$-CO-CH$_2$-NO$_2$, for example, 3-nitro-2-oxopropyl, 4-nitro-3-oxopropyl; -(CH$_2$)$_t$-CO-C$_n$H$_{2n}$-NH-COOA, for example, 4 -BOC-amino-2-oxobutyl, 5-BOC-amino-2-oxopentyl, 6-BOC-amino-2-oxohexyl; -C$_n$H$_{2n}$-CO-C$_n$H$_{2n}$-NH$_2$, for example 3-amino-2-oxopropyl, 4-amino-2-oxobutyl, 5-amino-2-oxopentyl, 6-amino-2-oxohexyl, 4 -amino-3-oxobutyl; -C$_n$H$_{2n}$-CO-NH-SO$_2$Ar, for example, N-phenylsulfonylcarbamoylmethyl; -C$_n$H$_{2n}$-C(=NR¹⁵)-A (preferably -CH$_2$-C(=NR¹⁵)-A such as -CH$_2$(=NOH)-CH$_3$, -CH$_2$-C(=NOCH$_3$)-C(CH$_3$)$_3$); -C$_n$H$_{2n}$-S-A, for example, methylthiomethyl; -C$_n$H$_{2n}$-SO-A, for example, methylsulfinylmethyl; -C$_n$H$_{2n}$-SO$_2$-A, for example, methylsulfonylmethyl; -C$_n$H$_{2n}$-S-Ar, for example, phenylthiomethyl; -C$_n$H$_{2n}$-SO-Ar, for example, phenylsulfinylmethyl; -C$_n$H$_{2n}$-SO$_2$-Ar, for example, phenylsulfonylmethyl, C$_n$H$_{2n}$-S-Het², for example, (2-thienyl) thiomethyl; -C$_n$H$_{2n}$-SO-Het², for example, (2 -pyridyl)-sulfinylmethyl; -C$_n$H$_{2n}$-SO$_2$-Het², for example, (2-, (3- or (4 -pyridyl)sulfonylmethyl; -CH(COOA)-Ar, for example, α-methoxycarbonylbenzyl, α-ethoxycarbonylbenzyl, α-isopropoxycarbonylbenzyl. The radical R³ can furthermore also be

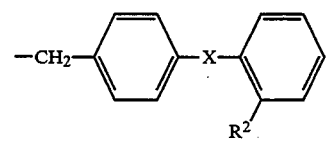

The radical R⁵ is preferably A, in particular methyl, ethyl, propyl or butyl; Ar, in particular phenyl; Het²-alkyl, in particular 2-, 3- or 4-pyridylmethyl; or cycloalkyl, in particular cyclopropyl.

The radical R⁶ is preferably H, or further A.

The radicals R⁷ and R⁸ are preferably in each case A.

The radicals R⁹ and R¹⁰ are preferably H or A, R⁹ is additionally preferably Ar, Ar-C$_n$H$_{2n}$ or Het².

Further preferred groups -NR⁹R¹⁰ are those in which R⁹ and R¹⁰ together are an alkylene chain having 2–5 C atoms, which can be substituted as indicated and/or interrupted by O or by -NR¹⁹. Particularly-preferred groups -NR⁹R¹⁰ of this type are, for example, aziridino, pyrrolidino, piperidino, morpholino, piperazino, 2-oxopyrrolidino, 2-alkoxycarbonylpyrrolidino (wherein the alkoxy group contains 1–4 C atoms) such as 2-methoxycarbonylpyrrolidino or 2-ethoxycarbonylpyrrolidino, 2- or 3-alkanoylaminopyrrolidino such as 2- or 3-acetamidopyrrolidino, 2-, 3- or in particular 4-oxopiperidino, 2-, 3- or in particular 4-Ar-piperidino such as 2-, 3- or 4-phenylpiperidino, 4-o-, 4-m- or 4-p-methoxyphenylpiperidino, 4-o-, 4-m- or 4-p-nitrophenylpiperidino, 4-o-, 4-m- pr 4-p-chlorophenylpiperidino, 3-hydroxy-methyl-4-p-chlorophenylpiperidino, 2-, 3- or 4-(2-thienyl)piperidino, 2-, 3- or 4-N,N-dimethylcarbamoylpiperidino, 2-, 3- or 4-N,N-diethylcarbamoylpiperidino, 2-, 3- or 4-benzoylpiperidino, 2-, 3- or 4-p-methoxybenzoylpiperidino, 4-methylpiperazino, 4-phenylpiperazino, 4-o-, 4-m- or 4-p-methoxyphenylpiperazino, 4-o-, 4-m- or 4-p-nitrophenylpiperazino, 4-o-, 4-m- or 4-p-chlorophenylpiperazino, 4- (2-pyrimidinyl) piperazino, 4 -methoxycarbonylpiperazino, 4-ethoxycarbonylpiperazino, 4-BOC-piperazino (BOC=butoxycarbonyl), 4-phenylsulfonylpiperazino, 4-p-tolylsulfonylpiperazino, 4-o-, 4-m- or 4-p-fluorophenylsulfonylpiperazino.

The radical $R^{11}$ preferably contains 1, 2 or 3 C atoms and is preferably methyl, ethyl, trifluoromethyl, pentafluoroethyl, 2,2,2-trifluoroethyl or 3,3,3-trifluoropropyl. If a compound of the formula I contains two radicals $R^5$, these can be identical to or different from one another.

$R^{12}$ is preferably Ar, -COOA, -COOK or -CO-NR$^9$R$^{10}$, or further preferably -CO-R$^{11}$, -CO-Ar, -CO-R$^{17}$ or -C(=NR$^{15}$)-A.

$R^{13}$ is preferably COOK or COOA.

$R^{14}$ is preferably Ar, in particular phenyl.

$R^{15}$ is preferably OH or OR$^{16}$ in particular OA.

$R^{16}$ is preferably A.

$R^{17}$ is preferably -C$_n$H$_{2n}$-NO$_2$ or -C$_n$H$_{2n}$-NR$^9$R$^{10}$, in particular -C$_n$H$_{2n}$-NH$_2$.

$R^{18}$ is preferably H, or further A having 1-4 C atoms.

$R^{19}$ is preferably H or A.

The parameter k is preferably 0 or 1. The parameter m is preferably 0 or 2. The parameter n is preferably 1, or further 2, 3 or 4.

Preferably, the radical X is absent or is -NH-CO- or -CO-NH-.

The radical Y is preferably O, or else S.

The compounds of the formula I can possess one or more chiral centers and can therefore exist in different forms (optically active or optically inactive). Formula I includes all these forms.

Accordingly the invention relates especially to those compounds of the formula I in which at least one of said radicals has one of the preferred meanings indicated above. Some preferred groups of compounds can be expressed by the following partial formulae Ia to Ic, which correspond to formula I and wherein the radicals not described more precisely are as defined in formula I, except that:

in Ia: X is absent;
in Ib: X is -NH-CO-;
in Ic: X is -CO-NH-.

Compounds of the formula Ia are particularly preferred.

The following are also preferred: compounds of the formulae Id and Iad to Icd, which correspond to the compounds of the formulae I and Ia to Ic, except that in addition Y is an O atom; compounds of the formulae Ie, Iae to Ide and Iade to Icde, which correspond to formulae I, Ia to Id and Iad to Icd, except that in addition R$^4$ is H; compounds of the formulae If, Iaf to Ief, Iaef to Idef and Iadef to Icdef, which correspond to formulae I, Ia to Ie, Iae to Ide and Iade to Icde, except that in addition R$^2$ is (a) -SO$_2$NH-COOA,
(b) -SO$_2$-NH-CO-Ar,
(c) -SO$_2$-NH-CO-cyclopropyl, or
(d) 4,5-dihydro-5-oxo-1,2,4-oxadiazol-3-yl.

Among these, preferred compounds are those in which R$^1$ is A or alkenyl each having 3-6 C atoms or cyclopropyl.

Other preferred groups of compounds correspond to the formula I and the other formulae given above, except that the radical R$^3$ is defined as follows:

(a) alkenyl-Ar with 2-6 C atoms in the "alkenyl" moiety
(b) -C$_n$H$_{2n}$-R$^{12}$,
(c) -C$_n$H$_{2n}$-Ar,
(d) -C$_n$H$_{2n}$-CO-NR$^9$R$^{10}$,
(e) -CH$_2$-CO-NR$^9$R$^{10}$ wherein R$^9$ and R$^{10}$ are each H, A or phenyl,
(f) CH$_2$-CO-NR$^9$R$^{10}$, wherein R$^9$ and R$^{10}$ together are an alkylene chain having 2-5 C atoms, which can be monosubstituted or polysubstituted by carbonyl oxygen, Ar, Het$^2$, -CO-Ar, -COOA, -CO-N(A)$_2$, -CH$_2$OH, -SO$_2$-Ar and/or -NH-CO-A and/or interrupted by O or by -NR$^{19}$,
(g) -CH$_2$-CO-NR$^9$R$^{10}$, wherein -NR$^9$R$^{10}$ is pyrrolidino, piperidino or morpholino,
(h) H,
(i) A,
(j) -CH$_2$Ar,
(k) -CH$_2$COOH,
(l) -CH$_2$COOA,
(m) -CH$_2$-CO-Ar,
(n) -CH$_2$-thienyl,
(o) cinnamyl,
(p) -CH(COOA)-Ar,
(q) -CH$_2$-S (O)$_m$-Ar,
(r) -CH$_2$-S-Ar,
(s) -CH$_2$-SO$_2$Ar.

The compounds of the formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially in European patent application A2-0 430 709 and U.S. Pat. No. 4,880,804), under conditions which are known and suitable for said reactions, it also being possible to make use of variants known per se, which are not mentioned in greater detail here.

If desired, the starting materials, in particular those of the formula IV, can also be formed in situ, so that they are not isolated from the reaction mixture but immediately reacted further to give the compounds of the formula I.

(a) The compounds of the formula I can preferably be obtained by reacting compounds of the formula II with compounds of the formula III. Particularly the biphenyl derivatives of the formula I (wherein X is absent) are readily obtainable in this way. In the compounds of the formula II, E is preferably Cl, Br, I or an OH group which has been functionally modified to acquire reactivity, such as alkylsulfonyloxy having 1-6 C atoms (preferably methylsulfonyloxy) or arylsulfonyloxy having 6-10 C atoms (preferably phenyl- or p-tolylsulfonyloxy). The reaction of II with III is conveniently carried out by first converting III to a salt by treatment with a base, for example with an alkali metal alcoholate such as CH$_3$ONa or potassium tert-butylate in an alcohol such as methanol or tert-butanol, or with an alkali metal carbonate such as K$_2$CO$_3$, or with an alkali metal hydride such as NaH, or with an alkali metal alcoholate in dimethylformamide (DMF), and then reacting said salt with II in an inert solvent, for example an amide such as DMF, N-methylpyrrolidone or dimethylacetamide, or a sulfoxide such as dimethyl sulfoxide (DMSO), conveniently at temperatures of preferably −20°-100°, especially 10°-30°. Other suitable bases are alkali metal hydrogen carbonates such as NaHCO$_3$ and KHCO$_3$.

(b) The compounds of the formula I can also be obtained by the cyclization of compounds of the formula IV. This cyclization is conveniently carried out by heating with polyphosphoric acid, acetic acid or diglyme to temperatures of preferably about 80–180, especially 120°–160°.

(c) Acid amides of the formula I (X=-NH-CO- or -CO- NH-) can also be obtained by reacting compounds of the formula V (or reactive derivatives thereof) with compounds of the formula VI (or reactive derivatives thereof). Suitable reactive derivatives of the carboxylic acids of the formulae V and VI ($X^1$ or $X^2$=COOH) are advantageously the corresponding chlorides, bromides or anhydrides. The reaction is conveniently carried out in the presence of an inert solvent, for example a halogenated hydrocarbon such as methylene chloride, chloroform, trichloroethene or 1,2-dichloroethane, or an ether such as tetrahydrofuran (THF) or dioxane, at temperatures of preferably about 0°–150°, especially 20°–80°. If acid halides are reacted, it is recommended to add a base, for example a tertiary amine such as triethylamine, pyridine or 4-dimethylaminopyridine.

(d) Reaction of a nitrile which corresponds to formula I but instead of the radical $R^2$ contains a CN group, with hydroxylamine yields the corresponding carboxamide oxime I, $R^2$=-C(NH$_2$)=NOH. This reaction is conveniently carried out in an inert solvent such as THF at temperatures of preferably about 20°–100°.

(e) Compounds of the formula I wherein $R^2$ is -SO$_2$NH-COOR$^5$, -SO$_2$NH-COR$^5$, -SO$_2$NH-SO$_2$R$^5$ or -SO$_2$NH-CONR$^5$R$^6$ can be obtained by n-acylation of compounds which correspond to the formula I but in which the radical $R^2$ is replaced by an -SO$_2$NH$_2$ group. Suitable acylating agents are, for example, compounds of the formulae E-COOR$^5$, for example methyl chloroformate and ethyl chloroformate; E-COR$^5$, for example acetyl chloride, cyclopropanecarbonyl chloride or benzoyl chloride; E-SO$_2$R$^5$, for example methanesulfonyl chloride, p-toluenesulfonyl chloride; E-CONR$^5$R$^6$, for example diphenylcarbamoyl chloride; O=C=NR$^5$ for example phenyl isocyanate. Normally, the reaction is performed in the presence of a base, preferably of a tertiary amine, for example triethylamine, pyridine or 4-dimethylaminopyridine, conveniently at temperatures of preferably about 0°–100°. An excess of the amine can also be used as a solvent. The reaction with isocyanates of the formula O=C=NR$^5$ to give the corresponding sulfonylureas is preferably performed at temperatures of about 50°–100°, an excess of the isocyanate being used as a solvent.

(f) It is furthermore possible to free a compound of the formula I from one of its functional derivatives by solvolysis (for example hydrolysis) or hydrogenolysis. Thus, carboxylic acids of the formula I which contain (at least) one COOH group can be obtained by the saponification of corresponding alkyl esters, for example with NaOH or KOH in aqueous solution, with or without the addition of an inert organic solvent such as methanol, ethanol, THF or dioxane, at temperatures of preferably about 0°–100°, or by the hydrogenolysis of corresponding benzyl esters, for example, on Pd-on-charcoal at pressures of preferably about 1–200 bar and at temperatures of preferably about 0°–100°, in one of the inert solvents indicated. It is also possible to cleave with alkali a compound which has the formula I but in which the radical $R^2$ is replaced by a 5-trichloromethyl-1,2,4-oxadiazol-3-yl group (which can be obtained by reacting a carboxamide oxime of the formula I, $R^2$=-C(NH$_2$)=NOH, with trichloroacetic anhydride), for example, with NaOH in water/dioxane at 0°–10° the corresponding compound I, $R^2$=4,5-dihydro-5-oxo-1,2,4-oxadiazol-3-yl, being obtained.

Some of the starting materials, especially those of the formulae II and VI, are known. If they are not known, they can be prepared by known methods analogously to known substances.

Compounds of the formula III (Y=O) can be obtained for example by reacting carboxylic acids of the formula $R^1$-COOH with compounds of the formula VII

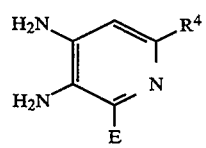

in the presence of polyphosphoric acid; the group E (preferably Cl) is hydrolyzed in the process and compounds of the formula III in which $R^3$=H are formed initially; these can then be reacted with compounds of the formula E-R$^3$ (wherein $R^3$ is different from H).

Compounds of the formula IV can be obtained for example by reacting compounds of the formula VIII

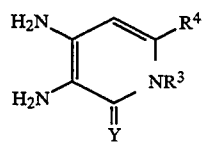

wherein, however, one of the amino groups is protected by an amino-protecting group (for example benzyl, A-O- CO- or benzyloxycarbonyl), with compounds of the formula II and subsequently cleaving the protecting group and reacting the products with acids of the formula $R^1$-COOH or functional derivatives thereof; they are not normally isolated, but are formed in situ in the last-mentioned reaction.

Compounds of the formula V can be prepared by reacting III with benzyl chlorides of the formula Cl-CH$_2$-p-C$_6$H$_4$X$^3$ (wherein $X^3$ is a protected NH$_2$ or COOH group) and subsequently cleaving the protecting group.

It is also possible to convert one compound of the formula I to another compound of the formula I by converting one or more of the radicals R and/or $R^2$ to other radicals R and/or $R^2$, for example by reacting a compound of the formula I($R^3$=H) with a compound of the formula E-R$^3$ (in which $R^3$ is different from H) or by reducing nitro groups to amino groups (for example by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOK groups, and/or oxidizing thioether groups to SO or SO$_2$ groups, for example with H$_2$O$_2$ or a peracid such as 3-chloroperbenzoic acid, and/or converting compounds of the formula I which contain a carbonyl group to compounds of the formula I which contain a -C(=NR$^{15}$) group, for example by reaction with a compound of the formula H$_2$N-R$^{15}$ such as ammonia, hydroxylamine, O-alkyl, O-alkenyl, O-alkynyl or O-arylhydroxylamines, cyanamide or primary amines of the formula H$_2$N-R$^{16}$, esterifying or amidating a carboxylic acid group, for example by reaction with an alcohol of the formula A-OH or with an amine of the formula HNR$^9$R$^{10}$ or of the formula H$_2$N-CHR$^{18}$-COOA, and/or converting a carbamidoxime group to a 4,5-dihydro-5-oxo-1,2,4-oxadiazol-3-yl group by reaction (a) with 1,1'-carbonyldiimidazole or anoalkyl chloroformate, (b) to a 4,5-dihydro-5-oxo-1,2,4-thiadiazol-3-yl group using 1,1'-thiocarbonyldiimidazole, (c) to a 2-oxo-3H-1,2,3,5-oxathiadiazol-4-yl group using SOCl$_2$ or (d) to a 2,2-dioxo-3H-1,2,3,5-oxathiadiazol-4-yl group using SO$_2$Cl$_2$, and/or converting an SO$_2$NH-COOR$^5$ group to an -SO$_2$NH-CO-NR$^5$R$^6$ group by amidation with a compound of the formula HNR$^5$R$^6$.

Compounds of the formula I (R$^3$=H) can thus be alkylated by reaction with compounds of the formula E-R$^3$. The reaction is preferably carried out in an inert solvent, for example an acid amide such as DMF, N-methylpyrrolidone, 1,3-dimethyl-2-oxohexahydropyrimidine or hexamethylphosphoramide, an alcohol such as methanol or tert-butanol, an ether such as THF or a halogenated hydrocarbon such as dichloromethane or mixtures thereof as solvents and/or in the presence of an alkali metal alcoholate such as sodium methylate or potassium tertbutylate, an alkali metal hydride such as sodium hydride or potassium hydride, an alkali metal carbonate such as sodium carbonate or potassium carbonate, an alkali metal bicarbonate such as sodium bicarbonate or potassium bicarbonate or a tertiary amine such as triethylamine or ethyldiisopropylamine at temperatures of preferably about −30–200, especially 20°–60°.

Furthermore, free amino groups can be acylated in conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of preferably about −60°14 +30° C.

If desired, a functionally modified amino and/or hydroxyl group in a compound of the formula I can be freed by solvolysis or hydrogenolysis using conventional methods. Thus, for example, a compound of the formula I containing an NHCOR$^5$ or COOA group can be converted to the corresponding compound of the formula I containing an NH$_2$ or HOOC group instead. COOA groups can be saponified for example with NaOH or KOH in water, water/THF or water/dioxane, at temperatures of preferably about 0°–100°.

The amidation of carboxylic acid groups is conveniently carried out according to customary methods of peptide synthesis, as are described, for example, in Houben-Weyl, L.c., volume 15/II, pages 1–806 (1974). The reaction is preferably carried out in the presence of a dehydrating agent, for example of a carbodiimide such as N,N'-dicyclohexylcarbodiimide ("DCCI"), 1,1'-carbonyldiimidazole or N-3-dimethylaminopropyl-N'-ethylcarbodiimide ("DAPECI"), or further propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as THF or dioxane, an amide such as DMF or dimethylacetamide, or a nitrile such as acetonitrile, at temperatures of preferably about −10–40, especially 0°–30°.

Instead of the carboxylic acids, suitable reactive derivatives of these substances can also be employed in the reaction, for example those in which reactive groups are intermediately blocked by protective groups. The acids can be used, for example, in the form of their activated esters, which are conveniently formed in situ, for example by addition of 1-hydroxybenzotriazole or N-hydroxysuccinimide.

The abovementioned conversions of a carbamidoxime group (I, R$^2$=-C(NH$_2$)=NOH) to various abovementioned heterocyclic radicals is preferably carried out in the presence of an inert solvent, for example of an ether such as THF, of a hydrocarbon such as toluene, of an amide such as DMF, of a halogenated hydrocarbon such as dichloromethane or of a base such as pyridine or of a mixture of two of these solvents at temperatures of preferably about 0°–100°.

A base of the formula I can be converted with an acid to the corresponding acid addition salt, for example by reaction of equivalent amounts of the base and of the acid in an inert solvent such as ethanol and subsequent evaporation. Possible acids for this reaction are especially those which yield physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compound of the formula I.

On the other hand, compounds of the formula I containing COOH or, for example, 1,2,4-oxadiazole groups can be converted with bases (for example sodium or potassium hydroxide or carbonate) to the corresponding metal salts, especially alkali metal or alkaline earth metal salts, or to the corresponding ammonium salts. The potassium salts of the 1,2,4-oxadiazole derivatives are particularly preferred.

The novel compounds of the formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; special lacquered tablets and capsules with coatings or shells resistant to gastric juices are of interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant gas mixture. It is convenient here to use the active ingredient in micronised form, it being possible for one or more additional physiologically compatible solvents, for example ethanol, to be present. Inhalation solutions can be administered with the aid of conventional inhalers. The novel compounds can be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colors and/or flavorings. If desired, they can also contain one or more other active ingredients, for example one or more vitamins, diuretics or antiphlogistics.

The substances according to the invention are normally administered analogously to other known, commercially available preparations, for example captopril or enalapril, but in particular analogously to the compounds described in U.S. Pat. No. 4 880 804, preferably in doses of about 1 mg–1 g, especially of 50–500 mg per dosage unit. The daily dose is preferably about 0.1–50 mg/kg, especially 1–10 mg/kg of body weight. However, the particular dose for each individual patient depends on a very wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in ° C. In the following examples, "conventional working-up" means: Water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

IP=imidazo[4,5-c]pyridine. Rf values on silica gel; eluent: dichloromethane/methanol 95:5.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 18 813.3, are hereby incorporated by reference.

EXAMPLES

Example 1

A mixture of 0.7 g of $K_2CO_3$, 3.04 g of 2-butyl-5-(N,N-diethylcarbamoylethyl) -4,5-dihydro-4-oxo-3H-IP (obtainable by condensation of valetic acid with 3,4-diamino-2 -chloropyridine in the presence of polyphosphoric acid to give 2-butyl-4,5-dihydro-4-oxo-1(or 3)H-IP, reaction with benzyl bromide in methanol in the presence of $CH_3ONa$ to give 3-benzyl-2-butyl-4,5-dihydro-4-oxo-3H-IP, reaction with N,N-diethylchloroacetamide in DMF in the presence of K-tert-butylate to give 3-benzyl-2-butyl-5-(N,N-diethylcarbamoylmethyl)-4,5-dihydro-4-oxy -3H-IP and hydrogenolytic removal of the benzyl group) and 30 ml of DMF is stirred for 1 hour at 20°. A solution of 3.31 g of 4-bromomethyl-2'-(4,5-dihydro-5-oxo-1,2,4-oxadiazol-3-yl)biphenyl (obtainable by reaction of 4-methyl-2'-cyanobiphenyl with hydroxylamine to give 4-methyl-2'-(aminooximinomethyl)biphenyl, reaction with ethyl chloroformate to give 4-methyl-2'-(4,5-dihydro-5-oxo-1,2,4-oxadiazol-3-yl)biphenyl and bromination) is then added dropwise at 0° with stirring in 35 ml of DMF. The mixture is stirred for 16 hours at 20°, evaporated, and worked up in the customary manner and 2-butyl-3-(2'-(4,5-dihydro-5-oxo-1,2,4-oxadiazol-3-yl) biphenyl-4-ylmethyl)-4,5-dihydro-4-oxo-5-(N,N-diethylcarbamoylmethyl)-3H-IP, m.p. 142°, is obtained. K salt, m.p. 275° (decomposition).

Example 2

A mixture of 1.02 g of valeric acid, 5 g of 4-amino-1,2-dihydro-2-oxo-3-(2'-(4,5-dihydro -5-oxo-1,2,4-oxadiazol-3-yl)biphenyl-4-ylmethyl-amino)-1-piperidinocarbonylmethyl)pyridine (obtainable by reaction of 3-amino-4-benzylamino-1,2- dihydro-2-oxo-1-piperidinocarbonylmethylpyridine with 4-bromomethyl-2'-(4,5-dihydro-5-oxo-1,2,4-oxadiazol-3-yl)biphenyl and hydrogenolytic removal of the benzyl group) and 50 g of polyphosphoric acid is heated for 5 hours at 140°. 4-Amino-1,2-dihydro-2-oxo-3-(N-(2'-(4,5-dihydro-5-oxo -1,2,4 -oxadiazol-3-yl)biphen-4-ylmethyl)-N-valerylamino)-1-piperidinocarbonylmethylpyridine and 1,2-dihydro-2-oxo-3-(2-(4,5-dihydro-5-oxo-1,2,4-oxadiazol-3-yl)biphen-4-ylmethylamino)-1-piperidinocarbonylmethyl-4-valerylaminopyridine are formed in situ as intermediates. The mixture is cooled, poured onto ice, rendered alkaline with sodium hydroxide solution and worked up in the customary manner and 2-butyl-3-(2'-(4,5-dihydro-5-oxo-1,2,4-oxadiazol-3-yl)biphenyl-4-ylmethyl)-4,5-dihydro-4-oxo-5-piperidinocarbonylmethyl-3H-IP is obtained. K salt, m.p. 284° (dec.).

Using
acetic acid
propionic acid
butyric acid
cyclopropanecarboxylic acid
Cyclopropaneacetic acid
instead of valeric acid the 3-(2'-(4,5-dihydro-5-oxo-1,2,4-oxadiazol-3-yl)biphenyl-4-ylmethyl) -4,5-dihydro-4-oxo-5-piperidinocarbonylmethyl-3H-IPs below are obtained analogously:
2-methyl-
2-ethyl- 2-propyl-
2-cyclopropyl-
2-cyclopropylmethyl-.

Example 3

A mixture of 3.86 g of 2-butyl-3-p-aminobenzyl -4,5-dihydro-4-oxo-5-benzyl-3H-IP (obtainable by reaction of 2-butyl-4,5-dihydro-4-oxo-5-benzyl-3H-IP with p-nitrobenzyl bromide to give 2-butyl-3-p-nitrobenzyl-4,5-dihydro-4-oxo-5-benzyl-3H-IP and subsequent reduction of the nitro group with HCl/Sn), 3 ml of triethylamine, 0.5 g of 4-dimethylaminopyridine and 120 ml of dichloromethane is cooled to 5° and treated dropwise with a solution of 2.25 g of o-(4,5-dihydro-5-oxo-1,2,4-oxadiazol -3-yl)benzoyl chloride in 20 ml of dichloromethane. The mixture is stirred for 16 hours at 20° evaporated and worked up in the customary manner and 2-butyl-3-p-(o -(4,5-dihydro-5-oxo-1,2,4-oxadiazol-3-yl)benzamido)benzyl-4,5-dihydro-4-oxo-5-benzyl-3H-IP is obtained.

Example 4

A mixture of 4.15 g of 2-butyl-3-p-carboxybenzyl -4,5-dihydro-4-oxo-5-benzyl-3H-IP, 12 g of thionyl chloride and 35 ml of CHCl$_3$ is boiled for 6 hours and then evaporated. The crude acid chloride obtained is freed from thionyl chloride residues by repeatedly dissolving in toluene and evaporating and is dissolved in 80 ml of THF. This solution is added dropwise to a solution of 1.77 g of 3-o-aminophenyl-4,5-dihydro-1,2,4-oxadiazol-5-one and 0.4 g of NaOH in 100 ml of water, and the mixture is stirred for 24 hours and worked up in the customary manner. 2-Butyl-3-(p-(o-(4,5-dihydro-5-oxo-1,2,4-oxadiazol -3-yl)anilinocarbonyl)benzyl)-4,5-dihydro-4-oxo-5-benzyl-3H-IP is obtained.

Example 5

(a) A solution 7.1 g of hydroxylammonium chloride in 30 ml of DMSO is treated with 14.4 ml of triethylamine in 40 ml of THF. The solution is filtered, and the filtrate is evaporated and treated with 3.82 g of 2-butyl-3-(2'-cyanobiphenyl-4-ylmethyl)-4,5-dihydro-4-oxo-3H-IP and a further 3.5 ml of triethylamine. The solution is stirred for 16 hours at 75°. It is cooled, poured into water, and the precipitated 2-Butyl-3-(2-(aminooximinomethyl)biphenyl -4-ylmethyl)-4,5-dihydro-4-oxo-3H-IP is filtered off and purified by chromatography. R$_f$0.28 (silica gel; methyl-tert-butyl ether/methanol 9:1).

(b) A suspension of 4.15 g of this compound in 32 ml of THF is treated with 2.4 g of 1,1'-carbonyldiimidazole and heated with stirring for 7 hours. The mixture is evaporated and worked up in the customary (ethyl acetate/dilute H$_2$SO$_4$), and 2-butyl-3-(2'-(4,5-dihydro-5-oxo -1,2,4-oxadiazole-3-yl) biphenyl-4-ylmethyl)-4,5 dihydro -4-oxo-3H-IP is obtained. M.p. 244°. K salt, m.p. 186°-190°.

2-Butyl-3-(2'-(aminooximinomethyl)biphenyl-4-ylmethyl)-4,5-dihydro-4-oxo-5-(N,N-diethylcarbamoylmethyl) -3H-IP, m.p 220°, is obtained from 2-butyl-3-(2'-cyanobiphenyl-4-ylmethyl)-4,5-dihydro-4-oxo-5-(N,N-diethylcarbamoylmethyl) -3H-IP analogously to (a) and 2-butyl-3-(2'-(4,5-dihydro-5-oxo-1,2,4-oxadiazol-3-yl) biphenyl-4-ylmethyl)-4,5-dihydro-4-oxo-5-(N,N-diethylcarbamoylmethyl)-3H-IP, m.p 142°, is obtained therefrom analogously to (b).

Example 6

(a) 550 mg of ethyl chloroformate are added to a solution of 526 mg of 2-butyl-3-(2'-aminosulfonylbiphenyl -4-ylmethyl)-4,5-dihydro-4-oxo-5-benzyl-3H-IP ["A"; m.p. 153°; obtainable by reaction of 2-butyl-4-oxo-4,5-dihydro-1(or 3)H-IP with 4'-bromomethylbiphenyl-N-tert-butyl -2-sulfonic acid to give 2-butyl-3-(2'-N-tert-butylaminosulfonylbiphenyl -4-ylmethyl)-4,5-dihydro-4-oxo-3H-IP ("B"; FAB 493), reaction with benzyl bromide/K tert-butanolate in DMF at 20° to give 2-butyl-3-(2'-N-tert-tert-butylaminosulfonylbiphenyl -4-ylmethyl)-4,5-dihydro-4-oxo-5-benzyl-3H-IP (m.p. 71°) and removal of the tertbutyl group using CF$_3$COOH/anisole] and 360 mg of 4-dimethylaminopyridine in 12 ml of pyridine, the mixture is stirred for 48 hours at 20°, 8 ml of methanol are added and it is worked up in the customary manner. 2-Butyl -3-(2'-(N-ethoxycarbonylaminosulfonyl)biphenyl-4-ylmethyl)-4,5-dihydro-4-oxo-5-benzyl-3H-IP is obtained. M.p. 95°.

2-Butyl-3-(2'-(N-butoxycarbonylaminosulfonyl)-biphenyl -4-ylmethyl)-4,5-dihydro-4-oxo-5-benzyl-3H-IP, m.p. 79°, is obtained analogously from "A" and butyl chloroformate.

The 2-butyl-3-(2'-(N-tert-butylaminosulfonyl)biphenyl -4-ylmethyl)-4,5-dihydro-4-oxo-5-R$^3$-3H-IPs below are obtained analogously from "B" using the appropriate halides (for example ethyl bromide):
-5-ethyl-
-5-carboxymethyl-
-5-methoxycarbonylmethyl-
-5-ethoxycarbonylmethyl-
-5-carbamoylmethyl-
-5-N,N-dimethylcarbamoylmethyl-
-5-N,N-diethylcarbamoylmethyl-
-5-N,N-diphenylcarbamoylmethyl-
-5-N-phenylcarbamoylmethyl-
-5-N-methyl-N-phenylcarbamoylmethyl-
-5-(2-oxo-3,3-dimethylbutyl)-
-5-phenacyl-
-5-(2-carboxyphenacyl)-
-5-(2-methoxyphenacyl)-
-5-pyrrolidinocarbonylmethyl-
-5-piperidinocarbonylmethyl-
-5-morpholinocarbonylmethyl-
-5-(2-methoxycarbonylbenzyl)-
-5-(2-ethoxycarbonylbenzyl)-
-5-(2-chlorobenzyl)-
-5-(2-chloro-6-nitrobenzyl)-
-5-(2-thienylmethyl)-
-5-cinnamyl-
-5-(α-methoxycarbonylbenzyl)-
-5-(α-isopropoxycarbonylbenzyl)-
-5-phenylthiomethyl-
-5-phenylsulfonylmethyl-,
therefrom the 2-butyl-3-(2'-(aminosulfonyl)biphenyl-4-ylmethyl) -4,5-dihydro-4-oxo-5-R$^3$-3H-IPs below:
-5-ethyl-
-5-carboxymethyl-
-5-methoxycarbonylmethyl
-5-ethoxycarbonylmethyl-
-5-carbamoylmethyl-
-5-N,N-dimethylcarbamoylmethyl-
-5-N,N-diethylcarbamoylmethyl-
-5-N,N-diphenylcarbamoylmethyl-
-5-N-phenylcarbamoylmethyl- -5-N-methyl-N-phenylcarbamoylmethyl-
-5-(2-oxo-3,3-dimethylbutyl)-
-5-phenacyl-
-5-(2-carboxyphenacyl)-
-5-(2-methoxyphenacyl)-
-5-pyrrolidinocarbonylmethyl-
-5-piperidinocarbonylmethyl-
-5-morpholinocarbonylmethyl-
-5-(2-methoxycarbonylbenzyl)-
-5-(2-ethoxycarbonylbenzyl)-
-5-(2-chlorobenzyl)-
-5-(2-chloro-6-nitrobenzyl)-
-5-(2-thienylmethyl)-
-5-(cinnamyl)-
-5-(α-methoxycarbonylbenzyl)-
-5-(α-isopropoxycarbonylbenzyl)-
-5-phenylthiomethyl-
-5-phenylsulfonylmethyl-,
and therefrom the 2-butyl-3-(2'-(N-butoxycarbonylaminosulfonyl) biphenyl-4-ylmethyl)-4,5-dihydro-4-oxo-5-$R^3$-3H-IPs below:
-5-ethyl-
-5-carboxymethyl-
-5-methoxycarbonylmethyl-
-5-ethoxycarbonylmethyl-
-5-carbamoylmethyl-
-5-N,N-dimethylcarbamoylmethyl-, m.p. 146°
-5-N,N-diethylcarbamoylmethyl-
-5-N,N-diphenylcarbamoylmethyl-, m.p. 92°
-5-N-phenylcarbamoylmethyl-
-5-N-methyl-N-phenylcarbamoylmethyl-
-5-(2-oxo-3,3-dimethylbutyl)-
-5-phenacyl-
-5-(2-carboxyphenacyl)-
-5-(2-methoxyphenacyl)-
-5-pyrrolidinocarbonylmethyl-
-5-piperidinocarbonylmethyl-
-5-morpholinocarbonylmethyl-,
-5-(2-methoxycarbonylbenzyl)-, m.p. 77°
-5-(2-ethoxycarbonylbenzyl)-
-5-(2-chlorobenzyl)-
-5-(2-chloro-6-nitrobenzyl)-
-5-(2-thienylmethyl)-
-5-cinnamyl-
-5-(α-methoxycarbonyl benzyl)-
-5-(α-isopropoxycarbonyl benzyl)-, m.p. 80°
-5-phenylthiomethyl-
-5-phenylsulfonylmethyl-.

The 2-butyl-3-(2'-$R^2$-biphenyl-4-ylmethyl)-4,5-dihydro-4-oxo-5-benzyl-3H-IPs below are obtained analogously using acetyl chloride, propionyl chloride, butyryl chloride, cyclopropanecarbonyl chloride, cyclopropaneacetyl chloride, cyclopentanecarbonyl chloride, benzoyl chloride, p-methoxybenzoyl chloride, p-chlorobenzoyl chloride or 2-thienylcarbonyl chloride instead of ethyl chloroformate:
-3-(2'-(acetylaminosulfonyl)biphenyl-4-ylmethyl)-
-3-(2'-(propionylaminosulfonyl)biphenyl-4-ylmethyl)-
-3-(2'-(butyrylaminosulfonyl)biphenyl-4-ylmethyl)-
-3-(2'-(cyclopropylcarbonylaminosulfonyl)biphenyl-4-ylmethyl)-, m.p. 142°
-3-(2'-(cyclopropylacetylaminosulfonyl)biphenyl-4-ylmethyl)-
-3-(2'-(cyclopentylcarbonylaminosulfonyl)biphenyl-4-ylmethyl)-
-3-(2'-(benzoylaminosulfonyl)biphenyl-4-ylmethyl)-
-3-(2'-(p-methoxybenzoylaminosulfonyl)biphenyl-4-ylmethyl)-
-3-(2'-(p-chlorobenzoylaminosulfonyl)biphenyl-4-ylmethyl)-
-3-(2'-(2-thienylcarbonylaminosulfonyl) biphenyl-4-ylmethyl)-.

Analogously, the 2-butyl-3-(2'-$R^2$-biphenyl-4-ylmethyl) -4,5-dihydro-4-oxo-5-$R^3$-3H-IPs below are obtained from the corresponding starting materials:
-3-(2'-(cyclopropylcarbonyl-aminosulfonyl)biphenyl-4ylmethyl)-5-(2-ethoxycarbonylbenzyl)-, m.p. 118°
-3-(2'-(benzoyl-aminosulfonyl)biphenyl-4-ylmethyl) -5-N,N-dimethylcarbamoylmethyl-, m.p. 209°
-3-(2'-(trifluoracetyl-aminosulfonyl)biphenyl-4methyl) -5-(2-chlorobenzyl)-m.p. 212°.

(b) A solution of 598 mg of the ethoxycarbonyl compound obtained as in (a) and 108 mg of 2-aminomethylpyridine in 30 ml of toluene is heated for 2 hours, cooled and worked up in the customary manner. 2-Butyl-3-(2'-N-(N-2-pyridylmethylcarbamoyl)aminosulfonylbiphenyl -4-ylmethyl)-4,5-dihydro-4-oxo-5-benzyl-3H-IP is obtained.

Example 7

A mixture of 526 mg of "A" and 7 ml of phenyl isocyanate is heated for 4 hours at 80°. It is cooled, the excess phenyl isocyanate is distilled off and 2-butyl-3-(2'-N-(N-phenylcarbamoyl)aminosulfonylbiphenyl-4-ylmethyl)-4,5-dihydro-4-oxo-5-benzyl-3H-IP is obtained after chromatographic purification.

Example 8

A solution of 4.41 g of 2-butyl-3-(2'-(4,5-dihydro-5-oxo-1,2,4-oxadiazol-3-yl)biphenyl-4-ylmethyl) -4,5-dihydro-4-oxo-3H-IP (see Example 5) in 35 ml of DMF is treated with 1.25 g of K tert-butylate with stirring at 20°. After stirring for 45 min, a solution of 1.27 g of benzyl chloride in 15 ml of DMF is added dropwise. The mixture is stirred for a further 16 hours at 20°, worked up in the customary manner and 2-butyl-3-(2'-(4,5-dihydro-5-oxo-1,2,4-oxadiazol-3-yl)biphenyl-4-ylmethyl) -4,5-dihydro-4-oxo-5-benzyl-3H-IP, m.p. 220° ("C"), is obtained.

The 2-butyl-3-(2'-(4,5-dihydro-5-oxo-1,2,4 oxadiazol-3-yl)biphenyl-4-ylmethyl)-4,5-dihydro-4-oxo-5-$R^3$-3H-IPs below are obtained analogously:
with ethyl iodide: -5-ethyl-
with bromoacetic acid: -5-carboxymethyl- ("E"), m.p. 203°
with methyl bromoacetate: -5-methoxycarbonylmethyl-
with ethyl bromoacetate: -5-ethoxycarbonylmethyl-
with tert-butyl bromoacetate: -5-tert-butoxycarbonylmethyl-, m.p. 168°; K salt, m.p. 219°
with bromoacetamide: -5-carbamoylmethyl-, m.p. 156°; K salt, m.p. 195°
with N,N-dimethylchloroacetamide: -5-N,N-dimethylcarbamoylmethyl-, Rf 0.25; K salt, 189°
with N,N-diethylchloroacetamide: -5-N,N-diethylcarbamoylmethyl-, M.p. 142°
with N,N-diphenylchloroacetamide: -5-N,N-diphenylcarbamoylmethyl-
with N-phenylchloroacetamide: -5-N-phenylcarbamoylmethyl-
with N-methyl-N-phenylchloroacetamide: -5-N-methyl-N-phenylcarbamoylmethyl-
with 2-oxo-3,3-dimethylbutylbromide: -5-(2-oxo-3,3-dimethylbutyl)-
with phenacyl bromide: -5-phenacyl-
with 2-carboxyphenacyl bromide: -5-(2-carboxyphenacyl)- with 2-methoxyphenacyl bromide: -5-(2-methoxyphenacyl)-
with bromoacetic acid pyrrolidide: -5-pyrrolidinocarbonylmethyl-
with bromoacetic acid piperidide: -5-piperidinocarbonylmethyl-, K salt, m.p. 284 ° (dec.)
with bromoacetic acid morpholide: -5-morpholinocarbonylmethyl-
with ethyl 2-bromomethylbenzoate: -5-(2-ethoxycarbonylbenzyl)-
with 2-chlorobenzyl bromide: -5-(2-chlorobenzyl)-
with 2-chloro-6-nitrobenzyl bromide: -5-(2-chloro-6-nitrobenzyl)-
with 2-thienylmethyl chloride: -5-(2-thienylmethyl)-
with cinnamyl bromide: -5-cinnamyl-
with methyl α-bromophenylacetate: -5-(α-methoxycarbonylbenzyl)-
with isopropyl α-bromophenylacetate: -5-(α-isopropoxycarbonylbenzyl)-, m.p. 175°
with phenylthiomethyl chloride: -5-phenylthiomethyl-
with α-bromophenylacetic acid piperidide: -5-(α-piperidinocarbonyl-benzyl)-, Rf 0.45; K salt, m.p. 193°
with phenylsulfonylmethyl chloride: -5-phenylsulfonylmethyl-
with 1-bromo-3-nitro-acetone: -5-(3-nitro-2-oxopropyl)-
with 6-BOC-amino-1-chloro-2-hexanone: -5-(6-BOC-amino-2-oxohexyl)-.

Example 9

A suspension of 0.7 g of 2-butyl-3-(2'-amino -oximinomethylbiphenyl-4-ylmethyl)-4,5-dihydro-4-oxo-5-benzyl-3H-IP ["D"; m.p. 224°; obtainable by reaction of 2-butyl-3-(2'-cyanobiphenyl-4-ylmethyl)-4-oxo-5-benzyl -4,5-dihydro-3H-imidazo[4,5-c]pyridine with hydroxylamine in ethanol/water] in 20 ml of toluene is treated with 0.13 ml of ethyl chloroformate and the mixture is stirred for 18 hours at 60°. 10 ml of DMF are then added, the mixture is stirred for a further 18 hours, 1.3 ml of 1N NaOH are then added, the mixture is boiled for 4 hours, cooled, adjusted to pH 4 and worked up in the customary manner and "C", m.p. 220°, is obtained.

Example 10

5.05 g of "D" are suspended under argon in 70 ml of pyridine and treated dropwise with stirring at 0° with a solution of 0.85 ml of $SOCl_2$ in 35 ml of $CH_2Cl_2$. The mixture is stirred for a further 2 hours at 0°, poured into 500 ml of water, worked up in the customary manner and 2-butyl-3-(2'-(2-oxo-3H-1,2,3,5-oxathiadiazol-4-yl)biphenyl-4-ylmethyl)-4,5-dihydro-4-oxo-5-benzyl-3H-IP is obtained.

Example 11

2-Butyl-3-(2'-(2,2-dioxo-3H-1,2,3,5-oxathiadiazol -4-yl)biphenyl-4-ylmethyl)-4,5-dihydro-4-oxo-5-benzyl-3H-IP is obtained from "D" and $SO_2Cl_2$ analogously to Example 10.

Example 12

A mixture of 505 mg of "D", 10 ml of THF and 180 mg of 1,1'-thiocarbonyldiimidazole is stirred for 30 min at 20° and evaporated. The residue is dissolved in ethyl acetate, washed with dilute hydrochloric acid and then with water, dried and evaporated again. The residue thus obtained is dissolved in a mixture of 60 ml of chloroform and 12 ml of methanol. 3.5 g of silica gel are added to this solution, the mixture is stirred for 48 hours at 20°, filtered and evaporated and the residue is purified by chromatography on silica gel. 2-Butyl-3-(2'-(4,5-dihydro-5-oxo-1,2,4-thiadiazol-3-yl)biphenyl-4-ylmethyl)-4,5-dihydro-4-oxo-5-benzyl-3H-IP is obtained.

Example 13

5.05 g of "D" are dissolved in 50 ml of dichloromethane, 1.15 g of triethylamine and 1.15 g of acetic anhydride are added and the mixture is stirred for 2 hours at 20°. It is evaporated and the residue is worked up in the customary manner (ethyl acetate/water; washing with $NaHCO_3$ solution) and the resulting crude acetyl derivative is dissolved in 30 ml of DMF. 4 g of $CS_2$ are added first, then, in the course of 10 minutes, NaH (60%, in oil; 1.4 g) and the mixture is stirred for 2 hours at 20°. After customary working up (pH 3, ice water), 2-butyl-3-(2'-(4,5-dihydro-5-thioxo-1,2,4-oxadiazol-3-yl)-biphenyl-4-ylmethyl)-4,5-dihydro-4-oxo-5-benzyl-3H-IP is obtained.

Example 14

1.5 ml of 1N NaOH is added dropwise with ice-cooling to a solution of 1 g of 2-butyl-3-(2'-(5-trichloromethyl -1,2,4-oxadiazol-3-yl)biphenyl-4-ylmethyl) -4,5-dihydro-4-oxo-5-benzyl-3H-IP (obtainable from 3-(4'-bromomethyl-2-biphenylyl)-5-trichloromethyl-1,2,4-oxadiazol (EP-A2-520423, Example 22 c) and 2-butyl-4,5-dihydro -4-oxo-5-benzyl-3H-IP analogously to Example 1) in a mixture of 8 ml of dioxane and 2 ml of water, the mixture is stirred for 30 min with ice-cooling and worked up as customary (dilute hydrochloric acid/ethyl acetate) and "C" is obtained, m.p. 220°.

Example 15

210 mg of DCCI are added to a solution of 499 mg of "E" in 14 ml of THF, the mixture is stirred for 10 min at 20°, 72 mg of pyrrolidine are added and the mixture is stirred for a further 18 hours at 20°. It is filtered, the filtrate is worked up in the customary manner, the crude product is chromatographed on silica gel (ethyl acetate/methanol 80:20) and 2-butyl-3-(2'-(4,5-dihydro-5-oxo-1,2,4-oxadiazol-3-yl)biphenyl-4-ylmethyl)-4,5-dihydro-4-oxo-5-pyrrolidinocarbonylmethyl -3H-IP is obtained.

Example 16

1.94 g of DAPECI, 1.36 g of 1-hydroxybenzotriazole and 1.1 ml of N-methylmorpholine are added successively to a solution of 5 g of "E" and 2.44 g of 1-p-fluorophenylsulfonylpiperazine in 90 ml of DMF, the mixture is stirred for 5 hours at 20°, the product is precipitated with water and filtered off, washed with water and dried, and 2-butyl-3-(2'-(4,5-dihydro-5-oxo -1,2,4-oxadiazol-3-yl)biphenyl-4-ylmethyl)-4,5-dihydro-4-oxo-5-(4-p-fluorophenylsulfonylpiperazinocarbonylmethyl) -3H-IP is obtained.

Example 17

A solution of 5 g of "E" in 20 ml of THF is added dropwise with stirring to a solution of 1.6 g of 1,1'-carbonyldiimidazole in 20 ml of THF and the mixture is then heated for 30 min. After cooling, 1.6 g of benzenesulfonamide are added, the mixture is stirred for 10m in, a solution of 1.48 g of 1,8-diazobicyclo[5.4.0]undec-7-ene in 10 ml of THF is added dropwise, the mixture is stirred for 18 hours at 20°, worked up in the customary manner (1N hydrochloric acid/dichloromethane) and 2-butyl-3-(2'-(4,5-dihydro-5-oxo-1,2,4-oxadiazol-3-yl)-biphenyl-4-ylmethyl)-4,5-dihydro-4-oxo-5-(N-phenylsulfonylcarbamoylmethyl) -3H-IP is obtained.

Example 18

A mixture of 1 g of 2-butyl-3-(2'-(4,5-dihydro-5-oxo-1,2,4-oxadiazol-3-yl)biphenyl-4-ylmethyl)-4,5-dihydro-4-oxo-5-ethoxycarbonylmethyl-3H-IP (ethyl ester of "E"), 12 ml of aqueous 2N NaOH solution and 48 ml of methanol is boiled for 2 hours, then evaporated. The residue is worked up with aqueous hydrochloric acid/dichloromethane in the customary manner and "E" is obtained; m.p. 203°.

Example 19

2-Butyl-3-(2'-(4,5-dihydro-5-oxo-1,2,4-oxadiazol -3-yl)biphenyl-4-ylmethyl)-4,5-dihydro-4-oxo-5-(N,N-diethylcarbamoylmethyl) -3H-IP, m.p. 142°, is obtained from 2-butyl-3-(2'-(4,5-dihydro-5-oxo-1,2,4-oxadiazol-3-yl)biphenyl-4-ylmethyl)-4,5-dihydro-4-oxo-3H-IP-acetic acid and diethylamine in the presence of DCCI analogously to Example 15.

Example 20

A solution of 1 g of 2-butyl-3-(2'-(4,5-dihydro -5-oxo-1,2,4-oxadiazol-3-yl)biphenyl-4-ylmethyl)-4,5-dihydro-4-oxo-5-(3-nitro-2-oxopropyl)-3H-IP in 20 ml of methanol is hydrogenated on 0.3 g of 5% Pd-carbon at 20° and normal pressure until the calculated amount of H₂ has been absorbed. The catalyst is filtered off, the filtrate is evaporated and 2-butyl-3-[2'-(2'-(4,5-dihydro-5-oxo -1,2,4-oxadiazol-3-yl)biphenyl-4-ylmethyl]-4,5-dihydro-4-oxo-5-(3-amino-2-oxopropyl)-3H-IP is obtained.

Example 21

A solution of 1 g of 2-butyl-3-(2'-(4,5-dihydro -5-oxo-1,2,4-oxadiazol-3-yl)biphenyl-4-ylmethyl)-4,5-dihydro-4-oxo-5-(6-BOC-amino-2-oxohexyl)-3H-IP in 20 ml of dichloromethane and 20 ml of trifluoroacetic acid is stirred for 1 hour at 20° and evaporated and the residue is worked up in the customary manner. 2-Butyl-3-(2'-(4,5-dihydro-5-oxo-1,2,4-oxadiazol-3-yl)biphenyl-4-ylmethyl) -4,5-dihydro-4-oxo-5-(6-amino-2-oxohexyl)-3H-IP is obtained.

The following examples relate to pharmaceutical formulations containing active ingredients of the formula I or their salts.

Example A: Tablets and coated tablets

Tablets of the following composition are produced by compression in conventional manner and, where required, are provided with a conventional sucrose-based coating:

| | |
|---|---|
| Active ingredient of the formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B: Hard gelatin capsules

Conventional two-part hard gelatin capsules are each filled with

| | |
|---|---|
| Active ingredient of the formula I | 100 mg |
| Lactose | 150 mg |
| Cellulose | 50 mg |
| Magnesium stearate | 6 mg |

Example C: Soft gelatin capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

Example E: Aqueous suspension for oral administration

An aqueous suspension of the active ingredient is prepared in conventional manner. The unit dose (5 ml) contains 100 mg of active ingredient, 100 mg of Na carboxymethylcellulose, 5 mg of Na benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine of formula I:

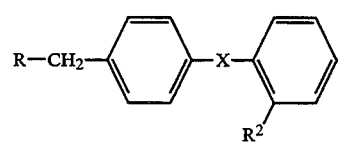

wherein

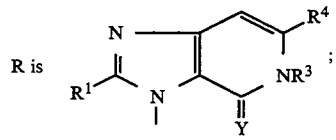

R¹ is A, $C_2-C_6$-alkenyl, $C_2-C_6$-alkynyl, $C_3-C_8$-cycloalkyl -$C_kH_{2k}$-, or $C_1-C_6$-alkyl in which a $CH_2$ group is replaced by O or S;

R² is -$SO_2NH$-$COOR^5$, -$SO_2NH$-$COR^5$, -$SO_2NH$-$SO_2R^5$, -$SO_2NH$-$CONR^5R^6$, -$C(NH_2)$=NOH, 4,5-dihydro-5-oxo -1,2,4-oxadiazol-3-yl, 4,5-dihydro 5-thioxo-1,2,4-oxadiazo-3-yl,2-oxo-3H-1,2,3,5-oxathiadiazol -4-yl, 2,2-dioxo-3H-1,2,3,5-oxathiadiazol -4-yl, 2,3-dihydro-3-oxo-1,2,4-oxadiazol-5-yl, 2,5-dihydro-2,5-dioxo-1H-imidazol-4-yl, 4,5-dihydro-5-oxo-1H-1,2,4-triazol-3-yl, 4,5-dihydro-5-thioxo-1H-1,2,4-triazol-3-yl, 2,3-dihydro-2-oxo-1,3,4-thiadiazol-5-yl or 4,5-dihydro-5-oxo-1,2,4-thiadiazol-3-yl;

R$^3$ is -C$_n$H$_{2n}$-R$^{12}$, CHR$^{13}$-C$_k$H$_{2k}$-R$^{14}$, or cinnamyl;

R$^4$ is H or Hal;

R$^5$ and R$^6$ are each, independently, H, C$_1$-C$_6$-alkyl wherein one CH$_2$ group can be replaced by O, or S or can contain a C-C double bond and which can additionally be substituted by OH, OR$^7$, Ar, Het$^2$, NR$^7$R$^8$, NR$^7$-COOR$^8$, NR$^7$-COO-C$_t$H$_{2t}$-Ar, NR$^2$-COO-C$_t$H$_{2t}$-Het$^2$ and/or COOR$^7$, or are C$_2$-C$_6$-cycloalkyl, CF$_3$, Ar or Het$^2$;

R$^7$ and R$^8$ are each, independently, A, C$_2$-C$_6$-alkenyl, C$_2$-C$_6$-alkynyl, C$_3$-C$_8$-cycloalkyl-C$_k$H$_{2k}$- or C$_1$-C$_6$-alkyl wherein one CH$_2$ group is replaced by O or S;

R$^9$ and R$^{10}$ are each, independently, H, A, C$_2$-C$_6$-alkenyl or C$_2$- C$_6$- alkynyl, Ar, ArC$_n$H$_{2n}$- or Her$^2$;

R$^9$ can also be -CH$_2$COOA, -SO$_2$-A or -SO$_2$-Ar;

R$^9$ and R$^{10}$ together can also be an alkylene chain having 2-5 C atoms, which can be monosubstituted or polysubstituted by carbonyl oxygen, Ar, Het$^2$, -CO-Ar, -COOA, -CO-N(A)$_2$, -CH$_2$OH, -SO$_2$-Ar and/or -NH-CO-A and/or interrupted by O or by -NR$^{19}$-;

R$^{11}$ is C$_1$-C$_5$-alkyl, wherein one or more H atoms can be replaced by F;

R$^{12}$ is Ar, Het$^1$, 1H-tetrazol-5-yl, -CO-NR$^9$R$^{10}$, -CO-R$^{17}$, -C(=NR$^{15}$)-A -C(=NR$^{15}$)-Het$^2$, -S(O)$_m$-A, -S(O)$_m$-Ar, -S(O)$_m$-Het$^2$, -SO$_2$-NH-Het$^2$ or -SO$_2$-OR$^{18}$;

R$^{13}$ is COOH, COOA, CONR$^9$R$^{10}$, CN, NO$_2$, NHCOR$^{14}$, NHSO$_2$R$^{14}$ or 1H-tetrazol-5-yl;

R$^{14}$ is Ar or cycloalkyl having 3-8 C atoms;

R$^{15}$ is H, OH, CN, R$^{16}$, OR$^{16}$ or OAr;

R$^{16}$ is A, C$_2$-C$_6$-alkenyl or C$_2$-C$_6$-alkynyl;

R$^{17}$ is -NH-CHR$^{18}$-COOH, -NH-CHR$^{18}$-COOA, -CH$_2$S(O)$_m$-Ar, -CH$_2$-COOA, -C$_n$H$_{2n}$-NHCOOA;

R$^{18}$ is H or A;

R$^{19}$ is H, A, Ar, COOA, Het$^2$ or SO$_2$-Ar;

X is absent or is -NH-CO- or -CO-NH-;

Y is O or S;

A is C$_1$-C$_6$-alkyl;

Ar is unsubstituted phenyl or phenyl monosubstituted or disubstituted by R$^{11}$, OH, OR$^{11}$, COOH, COOA, CN, NO$_2$, NH$_2$, NHA, N(A)$_2$, NHCOR$^{11}$, NHCOOA, NHSO$_2$R$^{11}$, Hal and/or 1H-tetrazol-5-yl;

Het$^1$ is a five- or six-membered saturated heterocyclic radical having 1 to 3 N, O and/or S atoms, which can be monosubstituted by carbonyl oxygen or =NR$^{15}$ and/or whose ring N atom(s) can in each case be substituted by A or Ar;

Het$^2$ is a five- or six-membered heteroaromatic radical having 1 to 3 N, O and/or S atoms, which is unsubstituted or substituted by one or more A groups and which can be fused with a benzene or pyridine ring;

Hal is F, Cl, Br or I;

k is 0, 1, 2, 3 or 4;

m is 0, 1 or 2;

n is 1, 2, 3, 4, 5 or 6; and t is 1, 2, 3 or 4; or a salt thereof.

2. A compound according to claim 1, wherein said compound is: 2-butyl-3-(2'-(4,5-dihydro-5-oxo-1,2,4-oxadiazol-3-yl)biphenyl-4-ylmethyl)-4-oxo-5-benzyl-4,5-dihydro-3H-imidazopyridine.

3. A compound according to claim 1, wherein X is absent.

4. A compound according to claim 1, wherein X is -NH-CO-.

5. A compound according to claim 1, wherein X is -CO-NH-.

6. A compound according to claim 1, wherein Y is O.

7. A compound according to claim 1, wherein R$^4$ is H.

8. A compound according to claim 1, wherein R$^2$ is -SO$_2$NH-COOA, -SO$_2$-NH-CO-Ar, -SO$_2$-NH-CO-cyclopropyl, or 4,5-dihydro-5-oxo-1,2,4-oxadiazol-3-yl.

9. A compound according to claim 8, wherein R$^1$ is A having 3-6 C atoms, alkenyl having 3-6 C atoms or cyclopropyl.

10. A compound according to claim 1, wherein R$^3$ is -C$_n$H$_{2n}$-R$^{12}$, cinnamyl or -CH(COOA)-Ar.

11. A compound according to claim 10, wherein R$^3$ is -C$_n$H$_{2n}$-Ar.

12. A compound according to claim 10, wherein R$^3$ is -CH$_2$-CO-NR$^9$R$^{10}$ wherein R$^9$ and R$^{10}$ are each H, A or phenyl.

13. A compound according to claim 10, wherein R$^3$ is -CH$_2$-CO-NR$^9$R$^{10}$ wherein R$^9$ and R$^{10}$ together are an alkylene chain having 2-5 C atoms, which can be monosubstituted or polysubstituted by carbonyl oxygen, Ar, Het$^2$, -CO-Ar, -COOA, -CO-N(A)$_2$, -CH$_2$OH, -SO$_2$-Ar and/or -NH-CO-A and/or interrupted by O or by -NR$^{19}$.

14. A compound according to claim 13, wherein -NR$^9$R$^{10}$ is pyrrolidinyl, piperidinyl or morpholinyl.

15. A compound according to claim 10, wherein R$^3$ is -CH$_2$-Ar, -CH$_2$-thienyl or -CH$_2$-S(O)$_m$-Ar.

16. A compound according to claim 15, wherein R$^3$ is -CH$_2$-S-Ar or -CH$_2$-SO$_2$-Ar.

17. A compound according to claim 10, wherein R$^3$ is cinnamyl.

18. A pharmaceutical composition comprising a compound according to claim 1 and a physiologically acceptable carrier.

19. A composition according to claim 18, wherein said compound is present in an amount of 1 mg-1 g.

20. A method of treatment or the prophylaxis of angiotensin(II)-dependent diseases or conditions, comprising administering a compound according to claim 1.

21. A method according to claim 20, wherein said disease is angiotensin(II)-dependent hypertension.

22. A method according to claim 21, wherein said compound is administered in a daily dosage of 0.1-100 mg/kg of body weight.

23. A compound according to claim 1, wherein R$^3$ is -CH$_2$-Ar or -CHR$^{13}$-Ar, R$^{13}$ is COOA or CONR$^9$R$^{10}$ and Ar is unsubstituted phenyl or phenyl monosubstituted by COOA or Hal.

24. A compound according to claim 1, wherein said compound is:

(a) 2-butyl-3-(2'-(N-butoxycarbonylaminosulfonyl)-biphenyl -4-methyl)-4,5-dihydro-4-oxo-5-benzyl-3H-imidazopyridine;

(b) 2-butyl-3-(2'-(N-(N-2-pyridylmethylcarbamoyl)aminosulfonyl) biphenylyl-4-methyl)-4,5-dihydro-4-oxo-5-benzyl-3H-imidazopyridine;

(c) 2-butyl-3-(2'-(N-butoxycarbonylaminosulfonyl)-biphenyl -4-methyl)-4,5-dihydro-4-oxo-5-(α-isopropoxycarbonylbenzyl) -3H-imidazopyridine;

(d) 2-butyl-3-(2'-(N-butoxycarbonylaminosulfonyl)-biphenyl -4-methyl)-4,5-dihydro-4-oxo-5-(2-methoxycarbonylbenzyl) -3H-imidazopyridine;

(e) 2-butyl-3-(2'-(cyclopropylcarbonylaminosulfonyl) -biphenylyl-4-methyl)-4,5-dihydro-4-oxo-5-(2-ethoxycarbonylbenzyl) -3H-imidazopyridine;

(f) 2-butyl-3-(2'-(trifluoroacetylaminosulfonyl)-biphenylyl -4-methyl)-4,5-dihydro-4-oxo-5-(2-chlorobenzyl)-3H-imidazopyridine;

(g) 2-butyl-3-(2'-(cyclopropylcarbonylaminosulfonyl) -biphenylyl-4-methyl)-4,5-dihydro-4-oxo-5-benzyl- 3H-imidazopyridine; or (h) 2-butyl-3-(2'-(N-ethoxycarbonylaminosulfonyl) -biphenylyl-4-methyl)-4,5-dihydro-4-oxo-5-benzyl-3H-imidazopyridine.

25. A compound according to claim 1, wherein $R^1$ is $-C_nH_{2n}-R^{12}$ or $-CHR^{13}-C_kH_{2k}-R^{14}$; $R^{12}$ is Ar, $Het^1$, 1H-tetrazol-5-yl, $-CO-NR^9R^{10}$, $-CO-R^{17}$, $-C(=NR^{15})$-A, $-C(=NR^{15})$-$Het^2$, $-S(O)_m$-A, $-S(O)_m$-Ar, $-S(O)_m$-$Het^2$, $-SO_2$-NH-$Het^2$ or $-SO_2$-$OR^{18}$; and $R^{13}$ is $CONR^9R^{10}$, CN, $NO_2$, $NHCOR^{14}$, $NHSO_2$, $R^{14}$ or 1H-tetrazol-5-yl.

26. A compound according to claim 1, wherein $R^{12}$ is Ar, $Het^1$, $-CO-NR^9R^{10}$, $-CO-R^{17}$, $-C(=NR^{15})$-A, $-C(=NR^{15})$-$Het^2$, $-S(O)_m$-A, $-S(O)_m$-Ar, $-S(O)_m$-$Het^2$, $-SO_2$-NH-$Het^2$ or $-SO_2$-$OR^{18}$.

27. A compound according to claim 5, wherein $R^{12}$ is Ar, $Het^1$, $-CO-NR^9R^{10}$, $-CO-R^{17}$, $-C(=NR^{15})$-A, $-C(=NR^{15})$-$Het^2$, $-S(O)_m$-A, $-S(O)_m$-Ar, $-S(O)_m$-$Het^2$, $-SO_2$-NH-$Het^2$ or $-SO_2$-$OR^{18}$.

28. An imidazopyridine of formula I:

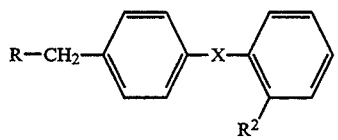

I wherein

R is

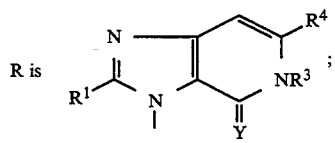

$R^1$ is A, $C_2$-$C_6$-alkenyl, $C_2$-$C_6$-alkynyl, $C_3$-$C_8$-cycloalkyl -$C_kH_{2k}$-, or $C_1$-$C_6$-alkyl in which a $CH_2$ group is replaced by O or S;

$R^2$ is $-SO_2NH$-$COOR^5$, $-SO_2NH$-$SO_2R^5$, $-C(NH_2)=NOH$, 4,5-dihydro -5-oxo-1,2,4-oxadiazol-3-yl, 4,5-dihydro-5-thioxo -1,2,4-oxadiazol-3-yl, 2-oxo-3H-1,2,3,5-oxathiadiazol -4-yl, 2,2-dioxo-3H-1,2,3,5-oxathiadiazol-4-yl, 2,3-dihydro-3-oxo-1,2,4-oxadiazol-5-yl, 2,5-dihydro-2,5-dioxo-1H-imidazol-4-yl, 4,5-dihydro-5-oxo-1H-1,2,4-triazol-3-yl, 4,5-dihydro-5-thioxo-1H-1,2,4-triazol-3-yl, 2,3-dihydro-2-oxo-1,3,4-thiadiazol-5-yl or 4,5-dihydro-5-oxo-1,2,4-thiadiazol-3-yl;

$R^3$ is H, $R^{11}$, $C_2$-$C_6$-alkenyl, $C_2$-$C_6$-alkynyl, $-C_nH_{2n}$-$R^{12}$, - $CHR^{13}$-$C_kH_{2k}$- $R^{14}$,

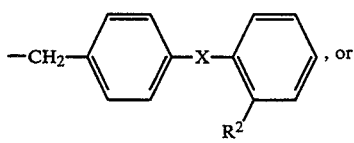

, or $C_2$-$C_6$-alkenyl monosubstituted or polysubstituted by COOH, COOA, CN, $NO_2$, $NR^9R^{10}$, $NHCOR^{11}$, $NHSO_2R^{11}$, Hal and/or Ar;

$R^4$ is H or Hal;

$R^5$ and $R^6$ are each, independently, H, $C_1$-$C_6$-alkyl wherein one $CH_2$ group can be replaced by O, or S or can contain a C-C double bond and which can additionally be substituted by OH, $OR^7$, Ar, $Het^2$, $NR^7R^8$, $NR^7$-$COOR^8$, $NR^7$-COO-$C_tH_{2t}$-Ar, $NR^7$-COO-$C_tH_{2t}$-$Het^2$ and/or $COOR^7$, or are $C_3$-$C_8$-cycloalkyl, $CF_3$, Ar or $Het^2$;

$R^7$ and $R^8$ are each, independently, A, $C_2$-$C_6$-alkenyl, $C_2$-$C_6$-alkynyl, $C_3$-$C_8$-Cycloalkyl-$C_kH_{2k}$- or $C_1$-$C_6$-alkyl wherein one $CH_2$ group is replaced by O or S;

$R^9$ and $R^{10}$ are each, independently, H, A, $C_2$-$C_6$-alkenyl or $C_2$-$C_6$-alkynyl, Ar, $ArC_nH_{2n}$- or $Het^2$;

$R^9$ can also be $-CH_2COOA$, $-SO_2$-A or $-SO_2$-Ar;

$R^9$ and $R^{10}$ together can also be an alkylene chain having 2-5 C atoms, which can be monosubstituted or polysubstituted by carbonyl oxygen, Ar, $Het^2$, -CO-Ar, -COOA, -CO-N(A)$_2$, -$CH_2OH$, -$SO_2$-Ar and/or -NH-CO-A and/or interrupted by O or by -$NR^{19}$-;

$R^{11}$ is $C_1$-$C_5$-alkyl, wherein one or more H atoms can be replaced by F;

$R^{12}$ is $C_3$-$C_8$-cycloalkyl, CN, COOA, COOH, Ar, $Het^1$, $Het^2$, 1H-tetrazol-5-yl, $-CO-NR^9R^{10}$, $-CO-R^{11}$, -CO-Ar, -CO-$Het^2$, -CO-$R^{17}$, $-C(=NR^{15})$-A, $-C(=NR^{15})$-$Het^2$, $-S(O)_m$-A, $-S(O)_m$-Ar, $-S(O)_m$-$Het^2$, $-SO_2$-NH-$Het^2$ or $-SO_2$-$OR^{18}$;

$R^{13}$ is COOH, COOA, $CONR^9R^{10}$, CN, $NO_2$, $NHCOR^{14}$, $NHSO_2R^{14}$ or 1H-tetrazol-5-yl;

$R^{14}$ is Ar or cycloalkyl having 3-8 C atoms;

$R^{15}$ is H, OH, CN, $R^{16}$, $OR^{16}$ or OAr;

$R^{16}$ is A, $C_2$-$C_6$-alkenyl or $C_2$-$C_6$-alkynyl;

$R^{17}$ is $-NH$-$CHR^{18}$-COOH, $-NH$-$CHR^{18}$-COOA, -$CH_2S(O)_m$-Ar, -$CH_2$-COOA, -$C_nH_{2n}$-NHCOOA;

$R^{18}$ ms H or A;

$R^{19}$ ms H, A, Ar, COOA, $Het^2$ or $SO_2$-Ar;

X is absent or is -NH-CO- or -CO-NH-;

Y is O or S;

A is $C_1$-$C_6$-alkyl;

Ar is unsubstituted phenyl or phenyl monosubstituted or disubstituted by $R^{11}$, OH, $OR^{11}$, COOH, COOA, CN, $NO_2$, $NH_2$, NHA, $N(A)_2$, $NHCOR^{11}$, NHCOOA, $NHSO_2R^{11}$, Hal and/or 1H-tetrazol-5-yl;

$Het^1$ is a five- or six-membered saturated heterocyclic radical having 1 to 3 N, O and/or S atoms, which can be monosubstituted by carbonyl oxygen or $=NR^{15}$ and/or whose ring N atom(s) can in each case be substituted by A or Ar;

$Het^2$ is a five- or six-membered heteroaromatic radical having 1 to 3 N, O and/or S atoms, which is unsubstituted or substituted by one or more A groups and which can be fused with a benzene or pyridine ring;

Hal is F, Cl, Br or I;

k is 0, 1, 2, 3 or 4;

is 0, 1 or 2;

n is 1, 2, 3, 4, 5 or 6; and t is 1, 2, 3 or 4; or a salt thereof.

29. A compound according to claim 28, wherein $R^2$ is $-C(NH_2)=NOH$, 4,5-dihydro-5-oxo-1,2,4-oxadiazol-3-yl, 4,5-dihydro -5-thioxo-1,2,4-oxadiazol-3-yl,2-oxo-3H-1,2,3,5-oxathiadiazol-4-yl, 2,2-dioxo-3H-1,2,3,5-oxathiadiazol-4-yl, 2,3-dihydro-3-oxo -1,2,4-oxadiazol-5-yl, 2,5-dihydro-2,5-dioxo-1H-imidazol-4-yl, 4,5-dihydro-5-oxo-1H-1,2,4-triazol-3-yl, 4,5-dihydro-5-thioxo-1H -1,2,4-triazol-3-yl, 2,3-dihydro-2-oxo-1,3,4-thiadiazol-5-yl or 4,5-dihydro-5-oxo-1,2,4-thiadiazol-3-yl.

30. A compound according to claim 29, wherein $R^2$ is 4,5-dihydro-5-oxo-1,2,4-oxadiazol-3-yl, 4,5-dihydro-5-thioxo-1,2,4 oxadiazol-3-yl, 2-oxo-3H-1,2,3,5-oxathiadiazol-4-yl, 2,2-dioxo-3H-1,2,3,5-oxathiadiazol-4-yl, 2,3-dihydro-3-oxo-1,2,4-oxadiazol-5-yl, 2,5-dihydro-2,5-dioxo-1H-imidazol-4-yl, 4,5-dihydro-5-oxo-1H-1,2,4-triazol-3-yl, 4,5-dihydro-5-thioxo-1H-1,2,4-triazol-3yl, 2,3-dihydro-2-oxo-1,3,4-thiadiazol-5-yl or 4,5-dihydro-5-oxo-1,2,4-thiadiazol-3-yl.

* * * * *